US011446435B2

(12) United States Patent
Cardinali et al.

(10) Patent No.: US 11,446,435 B2
(45) Date of Patent: Sep. 20, 2022

(54) DRUG DELIVERY SHUTTLE PUMP SYSTEM AND VALVE ASSEMBLY

(71) Applicant: Insulet Corporation, Acton, MA (US)

(72) Inventors: Steven Cardinali, Tewksbury, MA (US); Lucas McGahren, Boston, MA (US); Nicholas Lau, Boston, MA (US); Ian McLaughlin, Groton, MA (US)

(73) Assignee: INSULET CORPORATION, Acton, MA (US)

( * ) Notice: Subject to any disclaimer, the term of this patent is extended or adjusted under 35 U.S.C. 154(b) by 134 days.

(21) Appl. No.: 16/697,920

(22) Filed: Nov. 27, 2019

(65) Prior Publication Data

US 2020/0164143 A1    May 28, 2020

Related U.S. Application Data

(60) Provisional application No. 62/772,547, filed on Nov. 28, 2018.

(51) Int. Cl.
*A61M 5/168* (2006.01)
*A61M 5/142* (2006.01)
*A61M 5/145* (2006.01)

(52) U.S. Cl.
CPC .... *A61M 5/16881* (2013.01); *A61M 5/14244* (2013.01); *A61M 2005/14506* (2013.01); *A61M 2005/14533* (2013.01); *A61M 2205/0266* (2013.01)

(58) Field of Classification Search
CPC .......... A61M 5/16881; A61M 5/14244; A61M 2005/14506; A61M 2205/0266; A61M 3/0254; A61M 5/142; A61M 5/31593; A61M 5/16809; A61M 2005/14533; A61M 5/31595

See application file for complete search history.

(56) References Cited

U.S. PATENT DOCUMENTS

| 1,441,508 | A | 1/1923 | Jensen |
| 2,198,666 | A | 4/1940 | Gruskin |
| 2,752,918 | A | 7/1956 | Uytenbogaart et al. |

(Continued)

FOREIGN PATENT DOCUMENTS

| CA | 606281 A | 10/1960 |
| CN | 1375338 A | 10/2002 |

(Continued)

OTHER PUBLICATIONS

Schott web-page image from Jul. 9, 2016, https://www.us.schott.com/pharmaceutical_packaging/english/products/cartridges.html.

(Continued)

*Primary Examiner* — Nilay J Shah
(74) *Attorney, Agent, or Firm* — Goodwin Procter LLP

(57) ABSTRACT

A multiple pulse volume shuttle pump powered by a shape memory alloy (SMA) wire is disclosed. In some embodiments, a shuttle pump system may include a pump chamber, a valve operable with the pump chamber, and a wire coupled to a valve shaft of the valve for controlling a position of the valve. The shuttle pump system may further include a pin disposed within an inset pathway of a cam, wherein the pin is moveable between multiple positions of the inset pathway in response to actuation of the valve shaft.

9 Claims, 18 Drawing Sheets

(56) References Cited

U.S. PATENT DOCUMENTS

| | | |
|---|---|---|
| 3,176,712 A | 4/1965 | Ramsden |
| 3,297,260 A | 1/1967 | Barlow |
| 3,464,359 A | 9/1969 | King |
| 3,885,662 A | 5/1975 | Schaefer |
| 3,946,732 A | 3/1976 | Hurscham |
| 3,947,692 A | 3/1976 | Payne |
| 3,993,061 A | 11/1976 | OLeary |
| 4,108,177 A | 8/1978 | Pistor |
| 4,152,098 A | 5/1979 | Moody et al. |
| 4,210,173 A | 7/1980 | Choksi et al. |
| 4,221,219 A | 9/1980 | Tucker |
| 4,257,324 A | 3/1981 | Stefansson et al. |
| 4,268,150 A | 5/1981 | Chen |
| 4,313,439 A * | 2/1982 | Babb ............ A61M 5/172 604/28 |
| 4,371,790 A | 2/1983 | Manning et al. |
| 4,417,889 A | 11/1983 | Choi |
| 4,424,720 A | 1/1984 | Bucchianeri |
| 4,435,173 A | 3/1984 | Siposs et al. |
| 4,475,905 A * | 10/1984 | Himmelstrup .... A61M 5/31551 604/208 |
| 4,498,843 A | 2/1985 | Schneider et al. |
| 4,507,115 A | 3/1985 | Kambara et al. |
| 4,551,134 A | 11/1985 | Slavik et al. |
| 4,562,751 A | 1/1986 | Nason et al. |
| 4,567,549 A | 1/1986 | Lemme |
| 4,585,439 A | 4/1986 | Michel |
| 4,601,707 A | 7/1986 | Albisser et al. |
| 4,634,427 A | 1/1987 | Hannula et al. |
| 4,671,429 A | 6/1987 | Spaanderman et al. |
| 4,678,408 A | 7/1987 | Nason et al. |
| 4,684,368 A | 8/1987 | Kenyon |
| 4,685,903 A | 8/1987 | Cable et al. |
| 4,755,169 A | 7/1988 | Sarnoff et al. |
| 4,766,889 A | 8/1988 | Trick et al. |
| 4,808,161 A | 2/1989 | Kamen |
| 4,846,797 A | 7/1989 | Howson et al. |
| 4,858,619 A | 8/1989 | Toth |
| 4,898,579 A | 2/1990 | Groshong et al. |
| 4,908,017 A | 3/1990 | Howson et al. |
| 4,944,659 A | 7/1990 | Labbe et al. |
| 4,969,874 A | 11/1990 | Michel et al. |
| 4,991,743 A | 2/1991 | Walker |
| 5,007,458 A | 4/1991 | Marcus et al. |
| 5,020,325 A | 6/1991 | Henault |
| 5,062,841 A | 11/1991 | Siegel |
| 5,147,311 A | 9/1992 | Pickhard |
| 5,178,609 A | 1/1993 | Ishikawa |
| 5,205,819 A | 4/1993 | Ross et al. |
| 5,213,483 A | 5/1993 | Flaherty et al. |
| 5,222,362 A | 6/1993 | Maus et al. |
| 5,236,416 A | 8/1993 | McDaniel et al. |
| 5,261,882 A | 11/1993 | Sealfon |
| 5,261,884 A | 11/1993 | Stern et al. |
| 5,277,338 A | 1/1994 | Divall et al. |
| 5,281,202 A | 1/1994 | Weber et al. |
| 5,346,476 A | 9/1994 | Elson |
| 5,364,342 A | 11/1994 | Beuchat et al. |
| 5,388,615 A | 2/1995 | Edlund et al. |
| 5,433,710 A | 7/1995 | VanAntwerp et al. |
| 5,503,628 A | 4/1996 | Fetters et al. |
| 5,520,661 A | 5/1996 | Lal et al. |
| 5,533,389 A | 7/1996 | Kamen et al. |
| 5,582,593 A | 12/1996 | Hultman |
| 5,618,269 A * | 4/1997 | Jacobsen ............ A61M 5/16809 417/395 |
| 5,628,309 A | 5/1997 | Brown |
| 5,637,095 A | 6/1997 | Nason et al. |
| 5,665,070 A | 9/1997 | McPhee |
| 5,713,875 A | 2/1998 | Tanner, II |
| 5,747,350 A | 5/1998 | Sattler |
| 5,748,827 A | 5/1998 | Holl et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,807,075 A | 9/1998 | Jacobsen et al. |
| 5,839,467 A | 11/1998 | Saaski et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,957,890 A | 9/1999 | Mann et al. |
| 5,961,492 A | 10/1999 | Kriesel et al. |
| 5,971,963 A | 10/1999 | Choi |
| 6,019,747 A | 2/2000 | McPhee |
| 6,050,457 A | 4/2000 | Arnold et al. |
| 6,068,615 A | 5/2000 | Brown et al. |
| 6,086,615 A | 7/2000 | Wood et al. |
| 6,159,188 A | 12/2000 | Laibovitz et al. |
| 6,174,300 B1 | 1/2001 | Kriesel et al. |
| 6,190,359 B1 | 2/2001 | Heruth |
| 6,200,293 B1 | 3/2001 | Kriesel et al. |
| 6,352,522 B1 | 3/2002 | Kim et al. |
| 6,363,609 B1 | 4/2002 | Pickren |
| 6,375,638 B2 | 4/2002 | Nason et al. |
| 6,474,219 B2 | 11/2002 | Klitmose et al. |
| 6,485,461 B1 | 11/2002 | Mason et al. |
| 6,485,462 B1 | 11/2002 | Kriesel |
| 6,488,652 B1 | 12/2002 | Weijand et al. |
| 6,520,936 B1 | 2/2003 | Mann |
| 6,527,744 B1 | 3/2003 | Kriesel et al. |
| 6,537,249 B2 | 3/2003 | Kriesell et al. |
| 6,539,286 B1 | 3/2003 | Jiang |
| 6,569,115 B1 | 5/2003 | Barker et al. |
| 6,595,956 B1 | 7/2003 | Gross et al. |
| 6,656,158 B2 | 12/2003 | Mahoney et al. |
| 6,699,218 B2 | 3/2004 | Flaherty et al. |
| 6,723,072 B2 | 4/2004 | Flaherty et al. |
| 6,749,407 B2 | 6/2004 | Xie et al. |
| 6,851,260 B2 | 2/2005 | Mernoe |
| 6,883,778 B1 | 4/2005 | Newton et al. |
| 7,018,360 B2 | 3/2006 | Flaherty et al. |
| 7,104,275 B2 | 9/2006 | Dille |
| 7,128,727 B2 | 10/2006 | Flaherty et al. |
| 7,144,384 B2 | 12/2006 | Gorman et al. |
| 7,160,272 B1 | 1/2007 | Eyal et al. |
| 7,771,392 B2 | 8/2010 | De Polo et al. |
| 7,914,499 B2 | 3/2011 | Gonnelli et al. |
| 7,951,114 B2 * | 5/2011 | Rush ............ G01F 25/0007 604/151 |
| 8,267,921 B2 | 9/2012 | Yodfat et al. |
| 8,382,703 B1 | 2/2013 | Abdelaal |
| 8,499,913 B2 | 8/2013 | Gunter |
| 8,905,995 B2 | 12/2014 | Mernoe |
| 8,920,376 B2 | 12/2014 | Caffey et al. |
| 8,939,935 B2 | 1/2015 | OConnor et al. |
| 9,180,244 B2 | 11/2015 | Anderson et al. |
| 9,192,716 B2 | 11/2015 | Jugl et al. |
| 9,402,950 B2 | 8/2016 | Dilanni et al. |
| 9,539,596 B2 | 1/2017 | Ikushima |
| 10,441,723 B2 | 10/2019 | Nazzaro |
| 10,695,485 B2 | 6/2020 | Nazzaro |
| 2001/0016710 A1 | 8/2001 | Nason et al. |
| 2001/0056258 A1 | 12/2001 | Evans |
| 2002/0029018 A1 | 3/2002 | Jeffrey |
| 2002/0032374 A1 | 3/2002 | Holker et al. |
| 2002/0037221 A1 | 3/2002 | Mastrangelo et al. |
| 2002/0173769 A1 | 11/2002 | Gray et al. |
| 2002/0173830 A1 | 11/2002 | Starkweather et al. |
| 2003/0040715 A1 | 2/2003 | DAntonio et al. |
| 2003/0055380 A1 | 3/2003 | Flaherty |
| 2003/0097092 A1 | 5/2003 | Flaherty |
| 2003/0109827 A1 | 6/2003 | Lavi et al. |
| 2003/0163097 A1 | 8/2003 | Fleury et al. |
| 2003/0198558 A1 * | 10/2003 | Nason ............ F04B 19/006 417/53 |
| 2003/0199825 A1 | 10/2003 | Flaherty |
| 2004/0010207 A1 | 1/2004 | Flaherty et al. |
| 2004/0064088 A1 | 4/2004 | Gorman et al. |
| 2004/0068224 A1 | 4/2004 | Couvillon, Jr. et al. |
| 2004/0069044 A1 | 4/2004 | Lavi et al. |

(56) References Cited

U.S. PATENT DOCUMENTS

| | | |
|---|---|---|
| 2004/0092865 A1 | 5/2004 | Flaherty et al. |
| 2004/0094733 A1 | 5/2004 | Hower et al. |
| 2004/0153032 A1 | 8/2004 | Garribotto et al. |
| 2005/0020980 A1 | 1/2005 | Inoue et al. |
| 2005/0165363 A1 | 7/2005 | Judson et al. |
| 2005/0203461 A1 | 9/2005 | Flaherty et al. |
| 2005/0238507 A1 | 10/2005 | Dilanni et al. |
| 2005/0273059 A1 | 12/2005 | Mernoe |
| 2005/0277882 A1 | 12/2005 | Kriesel |
| 2006/0041229 A1 | 2/2006 | Garibotto et al. |
| 2006/0079765 A1 | 4/2006 | Neer et al. |
| 2006/0155210 A1 | 7/2006 | Beckman et al. |
| 2006/0173439 A1 | 8/2006 | Thorne et al. |
| 2006/0178633 A1 | 8/2006 | Garibotto et al. |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0073236 A1 | 3/2007 | Mernoe et al. |
| 2007/0088271 A1 | 4/2007 | Richards |
| 2007/0118405 A1 | 5/2007 | Campbell et al. |
| 2007/0282269 A1 | 12/2007 | Carter et al. |
| 2008/0004515 A1 | 1/2008 | Jennewine |
| 2008/0051738 A1 | 2/2008 | Griffin |
| 2008/0114304 A1 | 5/2008 | Nalesso et al. |
| 2008/0172028 A1 | 7/2008 | Blomquist |
| 2008/0243211 A1 | 10/2008 | Cartwright et al. |
| 2008/0294040 A1 | 11/2008 | Mohiuddin et al. |
| 2009/0024083 A1 | 1/2009 | Kriesel et al. |
| 2009/0062767 A1 | 3/2009 | Van Antwerp et al. |
| 2009/0198215 A1 | 8/2009 | Chong et al. |
| 2009/0278875 A1 | 11/2009 | Holm et al. |
| 2009/0326472 A1 | 12/2009 | Carter et al. |
| 2010/0036326 A1 | 2/2010 | Matusch |
| 2010/0152658 A1 | 6/2010 | Hanson et al. |
| 2010/0241066 A1 | 9/2010 | Hansen et al. |
| 2011/0054399 A1 | 3/2011 | Chong et al. |
| 2011/0073620 A1 | 3/2011 | Verrilli |
| 2011/0144586 A1 | 6/2011 | Michaud et al. |
| 2011/0180480 A1 | 7/2011 | Kloeffel et al. |
| 2011/0230833 A1 | 9/2011 | Landman et al. |
| 2012/0078161 A1 | 3/2012 | Masterson et al. |
| 2012/0172817 A1 | 7/2012 | Bruggemann et al. |
| 2012/0209207 A1 | 8/2012 | Gray et al. |
| 2013/0006213 A1 | 1/2013 | Arnitz et al. |
| 2013/0017099 A1 | 1/2013 | Genoud |
| 2013/0064701 A1 | 3/2013 | Konishi |
| 2013/0177455 A1 | 7/2013 | Kamen et al. |
| 2013/0178803 A1 | 7/2013 | Raab |
| 2013/0245545 A1 | 9/2013 | Arnold et al. |
| 2013/0267932 A1 | 10/2013 | Franke et al. |
| 2013/0296792 A1 | 11/2013 | Cabiri |
| 2014/0018730 A1 | 1/2014 | Muller-Pathle |
| 2014/0127048 A1 | 5/2014 | Dilanni et al. |
| 2014/0128839 A1 | 5/2014 | Dilanni et al. |
| 2014/0142508 A1 | 5/2014 | Dilanni et al. |
| 2014/0148784 A1 | 5/2014 | Anderson et al. |
| 2014/0171901 A1 | 6/2014 | Langsdorf et al. |
| 2015/0041498 A1 | 2/2015 | Kakiuchi et al. |
| 2015/0051487 A1 | 2/2015 | Uber et al. |
| 2015/0057613 A1 | 2/2015 | Clemente et al. |
| 2015/0064036 A1 | 3/2015 | Eberhard |
| 2015/0137017 A1 | 5/2015 | Ambrosina et al. |
| 2015/0202386 A1 | 7/2015 | Brady et al. |
| 2015/0290389 A1 | 10/2015 | Nessel |
| 2015/0297825 A1 | 10/2015 | Focht et al. |
| 2016/0008549 A1 | 1/2016 | Plumptre et al. |
| 2016/0025544 A1 | 1/2016 | Kamen |
| 2016/0055842 A1 | 2/2016 | DeFranks et al. |
| 2016/0082242 A1 | 3/2016 | Burton et al. |
| 2016/0129190 A1 | 5/2016 | Haitsuka |
| 2016/0193423 A1 | 7/2016 | Bilton |
| 2016/0213851 A1 | 7/2016 | Weibel et al. |
| 2017/0021096 A1 | 1/2017 | Cole et al. |
| 2017/0021137 A1 | 1/2017 | Cole |
| 2017/0100541 A1 | 4/2017 | Constantineau et al. |
| 2017/0216516 A1 | 8/2017 | Dale |
| 2017/0239415 A1 | 8/2017 | Hwang et al. |
| 2017/0290975 A1 | 10/2017 | Barmaimon et al. |
| 2018/0021521 A1 | 1/2018 | Sanchez |
| 2018/0185579 A1 | 7/2018 | Joseph et al. |
| 2018/0313346 A1 | 11/2018 | Oakes |
| 2019/0192782 A1 | 6/2019 | Pedersen et al. |
| 2019/0365993 A1 | 12/2019 | Staub et al. |
| 2020/0009315 A1 | 1/2020 | Brouet et al. |
| 2020/0345931 A1 | 11/2020 | Gray et al. |

FOREIGN PATENT DOCUMENTS

| | | | |
|---|---|---|---|
| CN | 102498292 B | 7/2015 | |
| CN | 204972511 U | 1/2016 | |
| CN | 105764543 B | 7/2016 | |
| CN | 206175149 U | 5/2017 | |
| CN | 107096091 A | 8/2017 | |
| CN | 108472441 A | 8/2018 | |
| DE | 4200595 A1 | 7/1993 | |
| DE | 19723648 C1 | 8/1998 | |
| DE | 102005040344 A1 | 3/2007 | |
| EP | 0454331 A1 | 10/1991 | |
| EP | 0789146 A1 | 8/1997 | |
| EP | 867196 A2 | 9/1998 | |
| EP | 1065378 A2 | 1/2001 | |
| EP | 1177802 A1 | 2/2002 | |
| EP | 1403519 A1 | 3/2004 | |
| EP | 2397181 A1 | 12/2011 | |
| EP | 2468338 A1 | 6/2012 | |
| EP | 2703024 A1 | 3/2014 | |
| EP | 2830499 A1 | 2/2015 | |
| FR | 2096275 A5 | 2/1972 | |
| FR | 2455269 A1 | 11/1980 | |
| FR | 2507637 A1 | 12/1982 | |
| FR | 2731475 A1 | 9/1996 | |
| GB | 357139 A | 9/1931 | |
| GB | 810488 A | 3/1959 | |
| GB | 875034 A | 8/1961 | |
| GB | 1204836 A | 9/1970 | |
| GB | 2008806 A | 6/1979 | |
| GB | 2077367 A | 12/1981 | |
| GB | 2456681 A | 7/2009 | |
| GB | 2549750 A | 11/2017 | |
| IL | 46017 A | 11/1977 | |
| JP | 06063133 A | 3/1994 | |
| JP | H06296690 A | 10/1994 | |
| JP | H08238324 A | 9/1996 | |
| JP | 2004247271 A | 9/2004 | |
| JP | 2004274719 A | 9/2004 | |
| JP | 2005188355 A | 7/2005 | |
| JP | 2006159228 A | 6/2006 | |
| JP | 6098988 B2 | 9/2006 | |
| JP | 2006249130 A | 9/2006 | |
| JP | 2009514580 A | 4/2009 | |
| JP | 2017513577 A | 6/2017 | |
| NL | 1019126 C1 | 4/2003 | |
| WO | 8101658 A1 | 6/1981 | |
| WO | 8606796 A1 | 11/1986 | |
| WO | WO-9320864 A1 * | 10/1993 | ................ F04B 7/06 |
| WO | 9415660 A1 | 7/1994 | |
| WO | 9855073 A1 | 12/1998 | |
| WO | 9856293 A1 | 12/1998 | |
| WO | 9910040 A1 | 3/1999 | |
| WO | 9910049 A1 | 3/1999 | |
| WO | 9962576 A1 | 12/1999 | |
| WO | 0029047 A1 | 5/2000 | |
| WO | 0178812 A1 | 10/2001 | |
| WO | 0220073 A2 | 3/2002 | |
| WO | 0226282 A2 | 4/2002 | |
| WO | 2002076535 A1 | 4/2002 | |
| WO | 2003097133 A1 | 4/2002 | |
| WO | 02068823 A1 | 9/2002 | |
| WO | WO-2004032994 A2 * | 4/2004 | ........ A61M 5/14244 |
| WO | 2004056412 A2 | 7/2004 | |
| WO | 2004110526 A1 | 12/2004 | |
| WO | 2007066152 A2 | 6/2007 | |
| WO | 2008133702 A1 | 11/2008 | |
| WO | 2009039203 A2 | 3/2009 | |

(56) References Cited

FOREIGN PATENT DOCUMENTS

| | | | |
|---|---|---|---|
| WO | 2009141005 A1 | 11/2009 | |
| WO | 2010022069 A2 | 2/2010 | |
| WO | 2010077279 A1 | 7/2010 | |
| WO | 2010139793 A1 | 12/2010 | |
| WO | 2011010198 A2 | 1/2011 | |
| WO | 2011031458 A1 | 3/2011 | |
| WO | 2011075042 A1 | 6/2011 | |
| WO | WO-2011069935 A2 * | 6/2011 | .......... A61M 5/3146 |
| WO | 2011133823 A1 | 10/2011 | |
| WO | 2012073032 A1 | 6/2012 | |
| WO | 2013050535 A2 | 4/2013 | |
| WO | 2013137893 A1 | 9/2013 | |
| WO | 2013149186 A1 | 10/2013 | |
| WO | 2014029416 A1 | 2/2014 | |
| WO | 2014149357 A1 | 9/2014 | |
| WO | 2014179774 A1 | 11/2014 | |
| WO | 2015032772 A1 | 3/2015 | |
| WO | 2015048791 A1 | 4/2015 | |
| WO | 2015081337 A2 | 6/2015 | |
| WO | 2015081337 A2 | 6/2015 | |
| WO | 2015117854 A1 | 8/2015 | |
| WO | 2015167201 A1 | 11/2015 | |
| WO | 2015177082 A1 | 11/2015 | |
| WO | 2017148855 A1 | 9/2017 | |
| WO | 2017187177 A1 | 11/2017 | |
| WO | 2021016452 A1 | 1/2021 | |

OTHER PUBLICATIONS

International Search Report and Written Opinion for Application No. PCT/US2019/059854, dated Aug. 26, 2020, 15 pages.
European Search Report and Written Opinion for the European Patent Application No. EP20174878, dated Sep. 29, 2020, 8 pages.
International Search Report and Written Opinion for PCT/US2018/014351, dated Jun. 4, 2018, 9 pages.
"Lind, et al. "Linear Motion Miniature Actuators."" Paper presented at the 2nd Tampere International Conference onMachine Automation, Tampere, Finland (Sep. 1998).
Author unknown, ""The Animas R-1000 Insulin Pump—Animas Corporation intends to exit the insulin pump businessand discontinue the manufacturing and sale of Animas® Vibe® and One Touch Ping® insulin pumps."" [online],Dec. 1999 [retrieved on Jan. 8, 2019]. Retrieved from the Internet URL: http://www. animaspatientsupport.com/.
Author unknown, CeramTec ""Discover the Electro Ceramic Products CeramTec acquired from Morgan AdvancedMaterials"" [online], Mar. 1, 2001 [retrieved on Jan. 8, 2019. Retrieved from the Internet URL: http://www.morgantechnicalceramics.com/.
Vaughan, M.E., ""The Design, Fabrication, and Modeling of a Piezoelectric Linear Motor."" Master's thesis,Virginia Polytechnic Institute and State University, VA. (2001).
Galante, et al., "Design, Modeling, and Performance of a High Force Piezoelectric Inchworm Motor," Journal of Intelligent Material Systems and Structures, vol. 10, 962-972 (1999).
International Search Report and Written Opinion for Interantional application No. PCT/US2017/055054, dated Jan. 25, 2018, 14 pages.
International Search Report and Written Opinion for International application No. PCT/US2018/045155, dated Oct. 15, 2018, 12 pages.
ISR/WO International Preliminary Report on Patentability for International application No. PCT/US2017/034811 dated Nov. 27, 2018 10 pages.
International Preliminary Report on Patentability for the International Patent Application No. PCT/US2017/046508 dated Feb. 12, 2019 10 pp.
International Search Report and Written Opinion for International application No. PCT/US2017/046508, dated Jan. 17, 2018, 14 pages.
International Search Report and Written Opinion for International application No. PCT/US2017/046777, dated Dec. 13, 2017, 14 pages.
International Search Report and Written Opinion for International application No. PCT/US2017/046737, dated Dec. 14, 2017, 11 pages.
International Search Report and Written Opinion for International application No. PCT/US2017/034814, dated Oct. 11, 2017, 16 pages.
European Search Report and Written Opinion for the European Patent Application No. EP19177571, dated Oct. 30, 2019, 8 pages.
ISR/WO International Preliminary Report on Patentability for the International Patent Application No. PCT/US 1814351, dated Aug. 1, 2019, 6 pages.
International Preliminary Report on Patentability for the International Patent Application No. PCT/US2017/046777, dated Feb. 19, 2019, 8 pages.
ISR/WO International Preliminary Report on Patentability for the International Patent Application No. PCT/US2017/046737, dated Feb. 19, 2019, 8 pages.
ISR/WO International Preliminary Report on Patentability for the International Patent Application No. PCT/US2017/055054,dated Apr. 9, 2019, 8 pages.
International Search Report and Written Opinion for application No. PCT/US2017/034811, dated Oct. 18, 2017, 15 pages.
EPO Search Report dated Nov. 11, 2015, received in corresponding Application No. 13768938.6, 7 pgs.
PCT International Search Report and Written Opinion dated Aug. 6, 2013, received in corresponding PCT Application No. PCT/US13/34674,pp. 1-19.
International Search Report and Written Opinion for International application No. PCT/GB2007/004073, dated Jan. 31, 2008.
International Search Report and Written Opinion for the International Patent Application No. PCT/US2019/063615, dated May 3, 2020, 16 pages.
International Preliminary Report on Patentability for the International Patent Application No. PCT/US2018/045155, dated Feb. 13, 2020, 10 pages.
International Search Report and Written Opinion for the International Patent Application No. PCT/US2019/035756, dated Jul. 31, 2019, 11 pages.
International Search Report and Written Opinion for the International Patent Application No. PCT/US2021/055581, dated Feb. 8, 2022, 19 pages.
International Search Report and Written Opinion for the International Patent Application No. PCT/US2022/011356, dated Apr. 29, 2022, 19 pages.
International Search Report and Written Opinion, Application No. PCT/US2022/016713, dated Aug. 5, 2022, 19 pages.

* cited by examiner

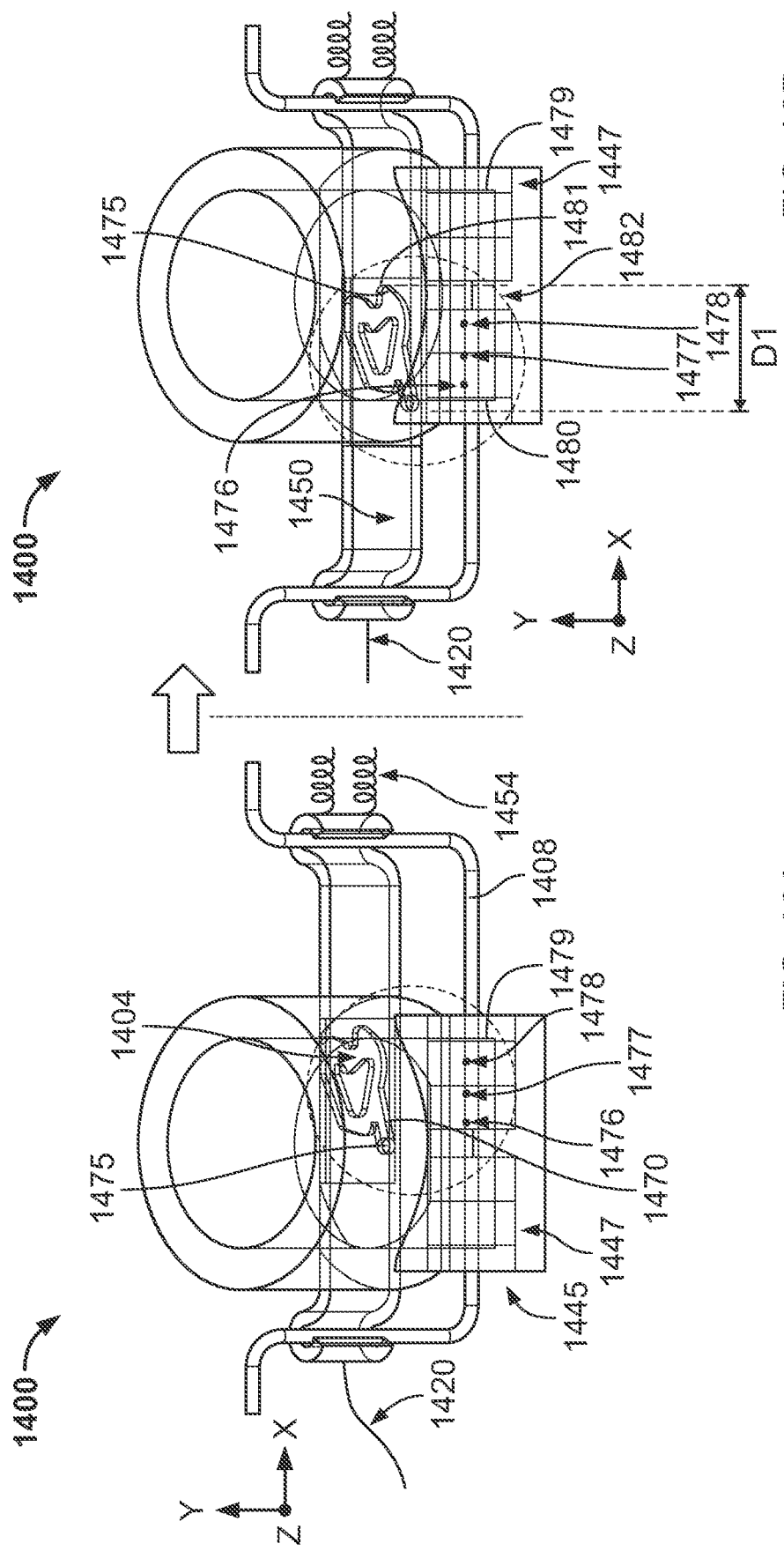

DRUG DELIVERY SHUTTLE PUMP SYSTEM AND VALVE ASSEMBLY

CROSS-REFERENCE TO RELATED APPLICATION

This application claims priority to U.S. Provisional Patent Application No. 62/772,547 filed Nov. 28, 2018, the entire contents of the application incorporated by reference herein.

TECHNICAL FIELD

Embodiments generally relate to a shuttle pump. More particularly, embodiments relate to a multiple pulse shuttle pump and valve assembly.

BACKGROUND

Many drug delivery devices use conventional reciprocating pumping mechanisms to deliver fluid from a reservoir to a user. These conventional reciprocating pumping mechanisms are typically one-to-one (1:1) reciprocating pumping mechanisms that accommodate miniaturization, thereby enabling the overall drug delivery device to be smaller and more compact.

Furthermore, current pumping mechanisms include a valve switch to allow the user to fill the reservoir and to dispense a fluid (e.g., insulin). The valve must be shut while the user fills the reservoir, and open when the pump begins working. The valve must also differentiate between filling and dispensing of the pump. This entails three states for the valve, e.g., closed, open for filling, and open for dispensing. However, due to the small size of the dimensions of these conventional pumps, precision tolerances for these conventional pumps are very difficult to meet in view of dosage accuracy requirements.

Therefore, there is a need for an improved pumping mechanism to use with reservoirs that can be made small and compact while achieving a desired dosage accuracy.

SUMMARY

In one approach of the disclosure, a shuttle pump system may include a pump chamber, a valve operable with the pump chamber, and a wire coupled to a valve shaft of the valve for controlling a position of the valve. The shuttle pump system may further include a pin disposed within an inset pathway of a cam, wherein the pin is moveable between multiple positions of the inset pathway in response to actuation of the valve shaft.

In another approach of the disclosure, a valve assembly may include a valve operable with a pump chamber, a wire coupled to a valve shaft of the valve for controlling a position of the valve, and a pin disposed within an inset pathway of a cam, wherein the pin is moveable between multiple positions of the inset pathway in response to actuation of the valve shaft.

In another approach of the disclosure, a wearable drug delivery system may include a pump chamber, a valve operable to control a fluid entering or exiting the pump chamber, and a wire coupled to a valve shaft of the valve for controlling a position of the valve, wherein the wire is a shape memory alloy (SMA) wire. The wearable drug delivery system may further include a pin disposed within an inset pathway of a cam, wherein the pin is moveable between multiple positions of the inset pathway in response to actuation of the valve shaft.

BRIEF DESCRIPTION OF THE DRAWINGS

The accompanying drawings illustrate example approaches of the disclosure, including the practical application of the principles thereof, as follows:

FIGS. 16A-16E demonstrate operation of the shuttle pump system of FIG. 14 according to embodiments of the present disclosure;

Figure 1:
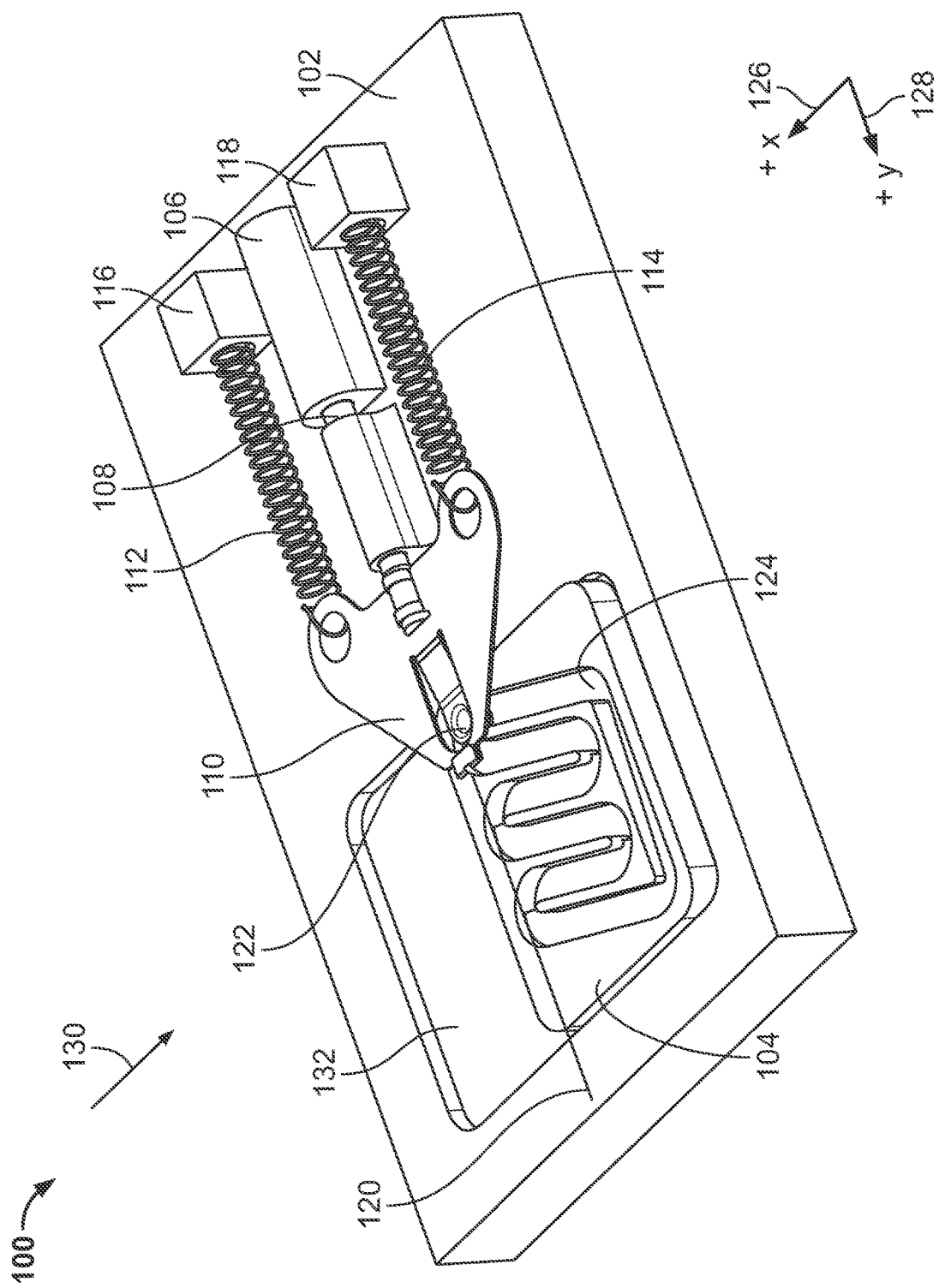
FIG. 1 illustrates a first exemplary embodiment of a multiple pulse shuttle pump system according to embodiments of the present disclosure.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, some reference numbers may be omitted in certain drawings.

DETAILED DESCRIPTION

This disclosure presents various systems, components, and methods for creating a multiple pulse volume shuttle pump operated by a wire. Each of the systems, components, and methods disclosed herein provides one or more advantages over conventional systems, components, and methods. The approaches herein may be embodied in many different forms and are not to be construed as being limited to the embodiments set forth herein. Instead, these embodiments are provided so this disclosure will be thorough and complete, and will fully convey the scope of the approaches to those skilled in the art.

Various embodiments include a multiple pulse volume shuttle pump. The shuttle pump can be powered by an SMA wire. The SMA wire can be coupled to a pumping piston of the shuttle pump. A pin can be coupled to a piston grip that can be coupled to the SMA wire and the pumping piston. The pin can be disposed within a path of a movement guide. As the SMA wire is sequentially activated and deactivated to pulse the SMA wire, the movement guide and the pin can move in response to extend a stroke length of the shuttle pump, thereby increasing the accuracy of the shuttle pump.

Various embodiments provide an approximately 3:1 to 5:1 reciprocating pump while enabling the use of an SMA wire. The pump can fully reset after 3-5 pulses according to various designs. The total wire stroke can be increased, for example, by the number of pulses per full cycle of the pump. As a result, the overall size of certain components of the pump system can be made larger without substantially increasing the overall size of the drug delivery device in which it is used. Further, the larger stroke results in improved volume accuracy as precision tolerances are less difficult to meet.

Various embodiments use a "push-push" mechanism to actuate between multiple states. For example, with the SMA wire, a valve goes from closed, open to filling, and open to dispensing. The user may the reservoir once for the device, so the closed state of the valve may only be employed during manufacturing. After a first actuation of the SMA wire, the mechanism cycles through the two open states for filling and dispensing. The SMA wire may be pulled against the frictional forces of valve and valve shaft, as well as return springs that hold the valve in the correct state while the SMA wire is inactive. In one non-limiting implementation, a bracket, which moves along a face of the piston chamber, is coupled to the SMA wire and to the valve shaft for actuating the valve between multiple states. Extruding from a wall of the piston chamber may be a pin operable to traverse a track of the bracket. The track and pin can be switched from either the bracket or the piston chamber interchangeably.

In another non-limiting implementation, a chamber contains a track along an interior wall of a cylinder defining the chamber. A pin may extend into the chamber, moving along the track to actuate the valve between multiple states. The pin may be an angled or bent needle, which is attached to a bracket. The bracket may be further coupled to the valve shaft, and therefore stabilizes both the pin and the valve shaft as the valve shaft switches between the different valve states. The bent needle and the valve shaft may move together linearly, wherein the bent needle follows the defined track as the chamber rotates. In some embodiments, a return spring holds the valve shaft in the different hold states.

FIG. 1 illustrates a first exemplary embodiment of a multiple pulse shuttle pump system (hereinafter "system"). The system 100 can include a base 102, a movement guide or cam block 104, a shuttle pump 106, a pumping piston 108, a piston grip 110, a first spring 112, a second spring 114, a first anchor or block 116, a second anchor or block 118, a wire 120 (e.g., a shape memory alloy (SMA)), and a pin 122. The arrangement and operation of the components of the system 100 can extend a stroke of the pumping piston 108, thereby allowing the shuttle pump 106 and its operation to be more accurate.

As shown in FIG. 1, the pumping piston 108 can be coupled to the piston grip 110. The piston grip 110 can be coupled to the first and second springs 112 and 114 which are in turn coupled to the first and second anchors 116 and 118, respectively. The pumping piston 108 is further coupled to the SMA wire 120. The SMA wire 120 can be coupled to a component (not shown in FIG. 1) for activating the SMA wire 120. The cam block 104 is positioned within a slot 132 of the base 102. The cam block 104 includes a path or pathway 124 in which the pin 122 can be disposed. The pin 122 can be coupled to or can be a part of the piston grip 110. A first axis 126 (e.g., x-axis) and a second axis 128 (e.g., y-axis) are shown for reference, with the first and second axes 126 and 128 being orthogonal to one another. As shown, the path 124 can be inset or carved into the cam block 104.

For simplicity, only a portion of the shuttle pump 106 is shown with the portion shown in a simplified manner for clarity. In general, the shuttle pump 106 can be coupled to a reservoir or chamber storing a fluid and can also be coupled to an exit port that can accept expelled fluid from the shuttle pump 106.

During operation, the SMA wire 120 can be activated to pull on the piston pump 108. The SMA wire 120 can attempt to move the piston pump 108 in a first direction parallel to the y-axis 128 away from the first and second anchors 116 and 118. When the SMA wire 120 is not activated, the SMA wire 120 can relax and the first and second springs 112 and 114 can attempt to move the piston pump 108 in a second direction (e.g., opposite the first direction) parallel to the y-axis 128 toward the first and second anchors 116 and 118.

Activation and deactivation of the SMA wire 120 can cause the pin 122 to traverse the path 124. To accommodate movement of the pin 122 through the path 124, the cam block 104 can move within the slot 132. In various embodiments, the cam block 104 can move in directions parallel to the x-axis 126 as the SMA wire 120 is alternatively activated and relaxed, thereby allowing the pin 122 (and the pumping piston 108) to move in directions parallel to the y-axis 128 while traversing the path 124. In general, operation of the system 100 causes the pin 122 (and the pumping piston 108) to move (e.g., linearly) in directions parallel to the y-axis 128 while the cam block moves in directions parallel to the x-axis 126.

A full stroke of the system 100 can correspond to the pin 122 traversing the entire path 124. Activation of the SMA wire 120 can correspond to a pulse of the system 100. For each pulse, the pin 122 traverses a portion of the path 124. A portion of the full stroke of the system 100 can correspond to the pin traversing a portion of the path 124. The path 124, as described herein, can be shaped and/or can have features to provide designated positions or states of the pin 122 corresponding to each pulse. Sequential activation and deactivation of the SMA wire 120, as described herein, can extend or make longer the stroke of the piston pump 108.

Figure 2:
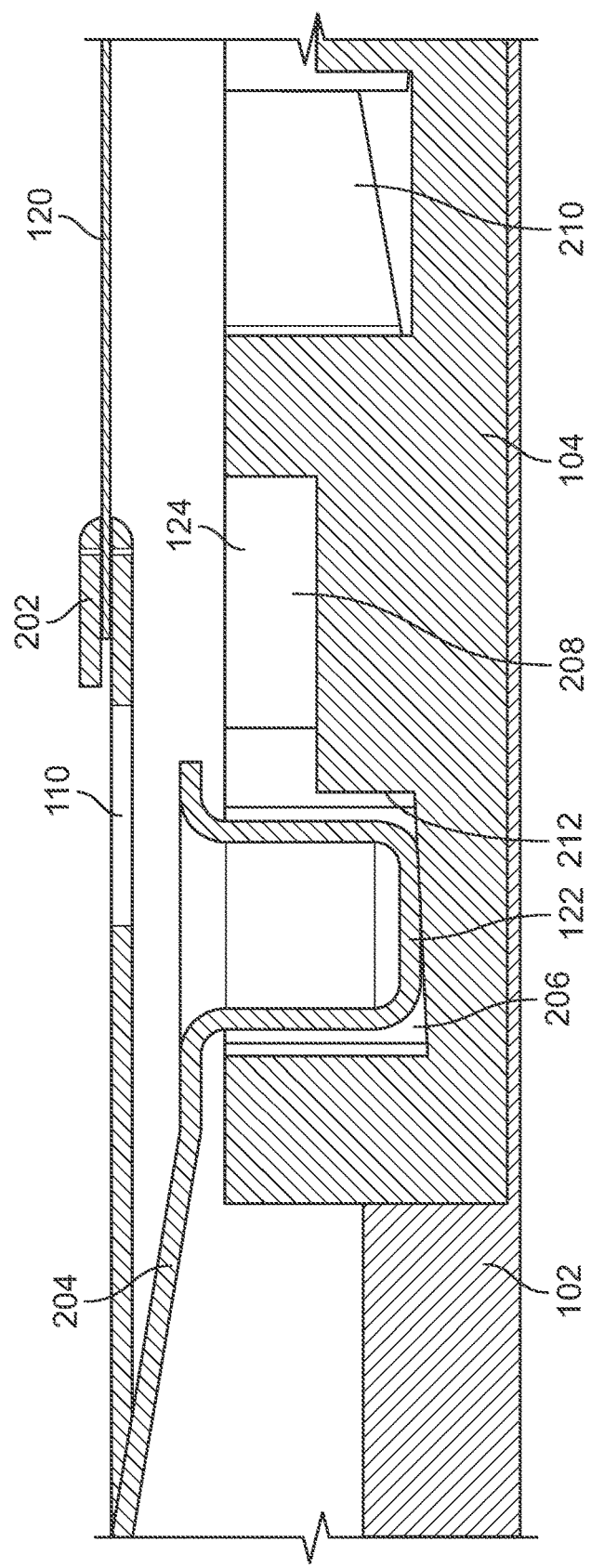
FIG. 2 illustrates a cross-sectional side view of a portion of the multiple pulse shuttle pump system of FIG. 1 according to embodiments of the present disclosure.

Reference element 130 represents a point of view of the system 100 shown in FIG. 2. FIG. 1 can represent a first view of the system 100.

FIG. 2 illustrates a second view of the system 100 (or a portion thereof). FIG. 2 can represent a cross-sectional side view of the system 100 (or a portion thereof) as viewed from the point of view 130 shown in FIG. 1. As shown, the pin 122 is disposed within the path 124, which can include a first path portion 206, a second path portion 208, and a third path portion 210. The pin 122 can be positioned within the first path portion 206 and can be restricted from moving into the second path portion 208 by a drop off or ledge 212. The drop off 212 can be an example of a feature of the path 124 that can ensure movement of the pin 122 in a certain direction within the path 124. In various embodiments, the pin 122 can traverse from the second path portion 208 to the first path portion 206 in a desired manner and then be restricted from moving back (e.g., backwards) into the second path portion 208.

As further shown in FIG. 2, a connection or coupling 202 is provided to connect the SMA wire 120 to the piston grip 110. Any type of connection or coupling 202 can be used. The piston grip 110 can include a finger spring 204 coupled to the pin 122. The finger spring 204 can allow the pin 122 to move (e.g., up and down relative to the depiction of the pin in FIG. 2) to traverse the shapes and/or features of the path 124 as described herein.

Figure 3:
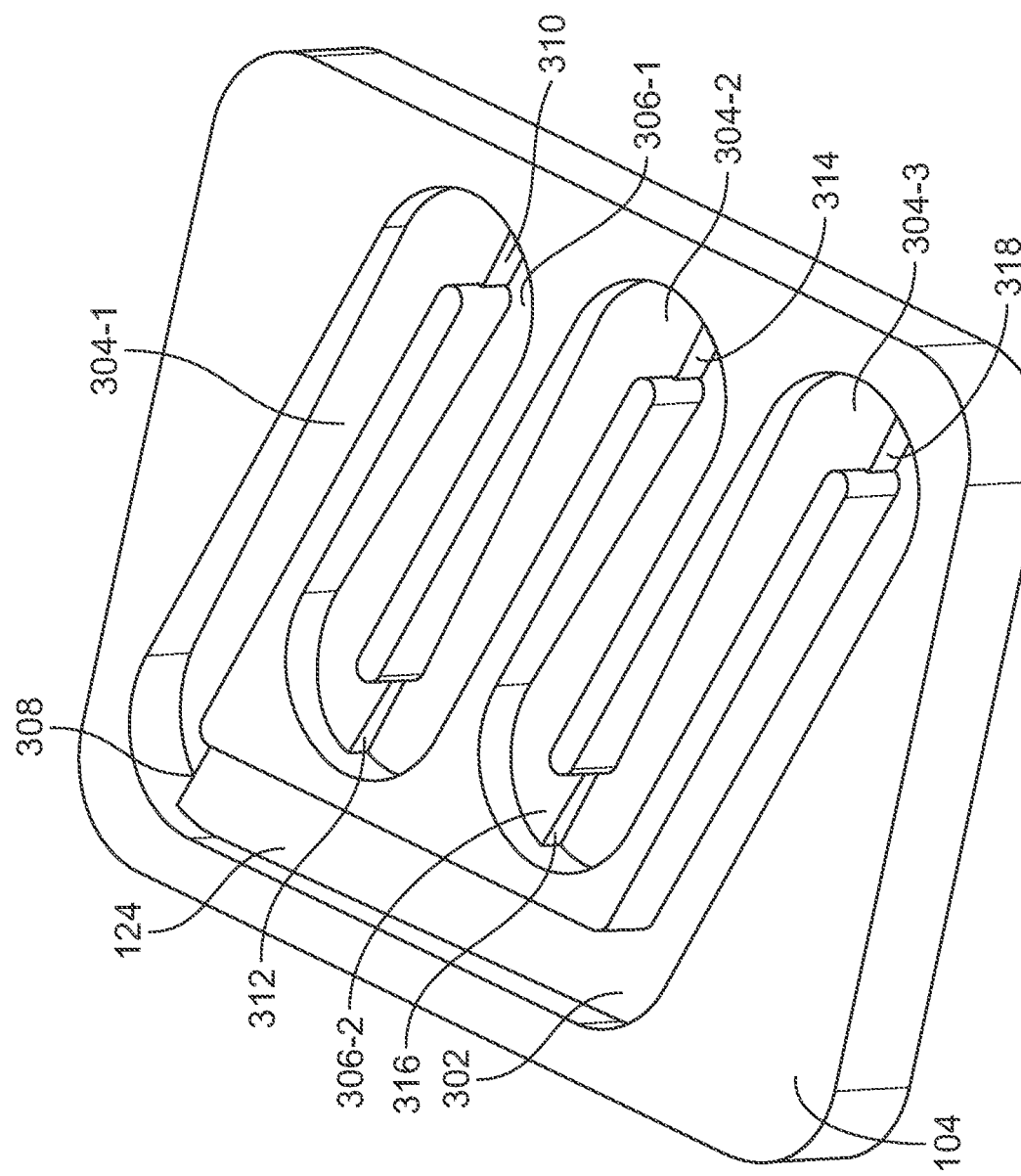
FIG. 3 illustrates a cam block of the multiple pulse shuttle pump system of FIG. 1 according to embodiments of the present disclosure.

FIG. 3 illustrates the cam block 104. As shown, the path 124 can include different sections. A first section 302 can represent a first portion of the path 124. As the pin 122 travels along the first section 302, the pumping piston 108 can be open to a reservoir that stores a fluid. Accordingly, as the pin traverses the first section 302, the pumping piston 108 can be reloaded with a fluid stored in the reservoir. The first section 302 can be sloped—for example, to form a ramp. A first drop off 308 can be positioned between the first section 302 and a second section 304-1 of the path 124. The first drop off 308 can be formed by or can be positioned at the interface of the first section 302 and the second section 304-1.

As further shown in FIG. 3, the path 124 can include a third section 306-1, a fourth section 304-2, a fifth section 306-2, and a sixth section 304-3. The second, fourth, and sixth sections 304-1, 304-2, and 304-3 can be similarly shaped and/or sloped. That is, the second, fourth, and sixth sections 304-1, 304-2, and 304-3 can each form inclines or ramps oriented in the same direction. The third and fifth sections 306-1 and 306-2 can be similarly shaped and/or sloped, for example, in a manner opposite to the shaping and/or sloping of the second, fourth, and sixth sections 304-1, 304-2, and 304-3. As the pin 122 traverses the second section 304-1, the third section 306-1, the fourth section 304-2, the fifth section 306-2, and the sixth section 304-3, the piston pump 108 can be open to a port that can provide liquid expelled from the piston pump 108 to a delivery system.

The interface between sequential or adjacent sections can include drop offs to guide movement of the pin 122 as it traverses the path 124. Along with the first drop off 308, a second drop off 310 can be positioned between the sections 304-1 and 306-1, a third drop off 312 can be positioned between sections 306-1 and 304-2, a fourth drop off 314 can be positioned between sections 304-2 and 306-2, a fifth drop off 316 can be positioned between sections 306-2 and 304-3, and a sixth drop off 318 can be positioned between the sections 304-3 and 302.

The sloping of the different sections of the path 124 and the drop offs positioned between the different sections of the path 124 can ensure the pin 122 traverses a desired route along the path based on the sequential activation/deactivation of the SMA wire 120. For example, after traversing the section 304-1, the pin 122 can fall down from the elevated portion of the section 304-1 into the lowered portion of the section 306-1—with the interface between the elevated portion of the section 304-1 and the lowered portion of the section 306-1 forming the drop off 310. The drop 310 can prevent the pin 122 from traveling from the section 306-1 back into the section 304-1.

Figure 4:
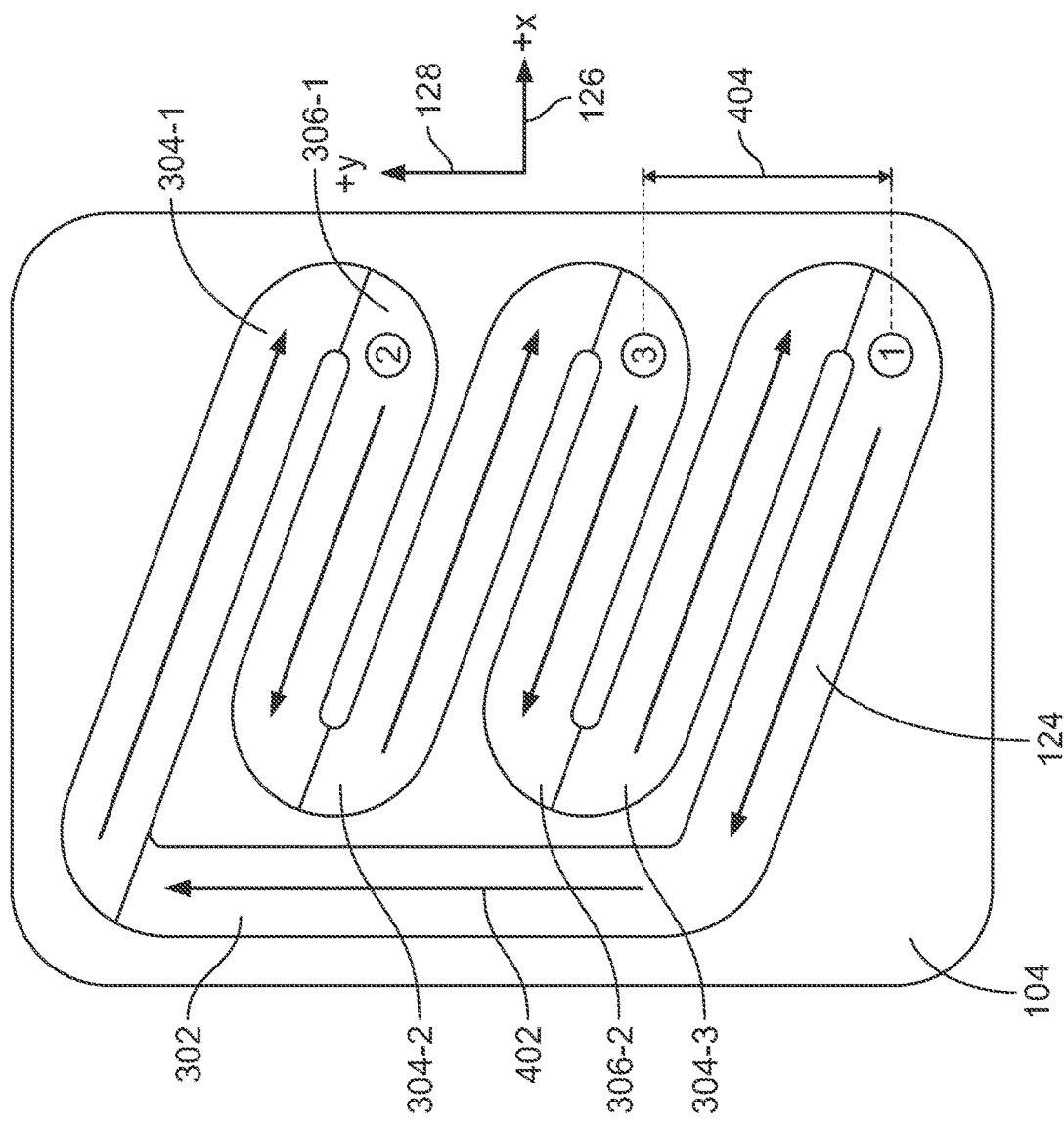
FIG. 4 illustrates an overhead view of the cam block of FIG. 3 according to embodiments of the present disclosure.

FIG. 4 illustrates an overhead view of the cam block 104. As shown, FIG. 4 includes a route 402 of the pin 122 (e.g., as indicated by the sequence of arrows collectively referenced by the route label 402). In various embodiments, the SMA wire 120 can be sequentially activated and deactivated to cause the pin 122, in conjunction with associated movement of the cam block 104, to traverse the route 402 of the path 124. As an example, the pin 122 can traverse the section 302, then the section 304-1, then the section 306-1, then the section 304-2, then the section 306-2, and then the section 304-3 before returning to the section 302. In various embodiments, a full stroke of the system 100 corresponds to the pin 122 starting at an initial position, labeled as "1" in FIG. 4, and returning to the initial "1" position.

The route 402 traversed by the pin 122 can be broken into multiple pulses. Based on control of the SMA wire 120 in relation to the features provided by the path 124, the route 402 traversed by the pin 122 can be broken into two or more pulses. In an embodiment, the route 402 traversed by the pin 122 can be broken into three or more pulses. Each pulse can correspond to the SMA wire 120 being activated (e.g., after being relaxed). Additional positions or states of the pin 122 are further indicated by the subsequent positions, labeled "2" and "3" in FIG. 4. In an embodiment, position "2" can represent a position of the pin 122 after second and third pulses of the SMA wire 120. Further, a distance between the pin 122 positions can represent the stroke of each pulse of the system 100. For example, a distance 404 can represent a stroke of a pulse between position "2" and position "3," for example, between second and third pulses. As shown, the distance 402 is along the y-axis 128. Similar distances between the other indicated positions can be determined to provide the full stroke of the system 100.

Figure 5:
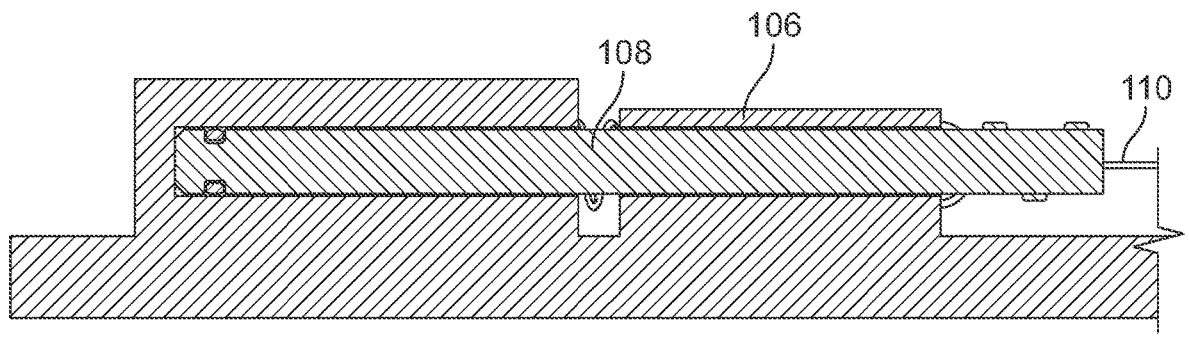
FIG. 5 illustrates a side view of the shuttle pump of the multiple pulse shuttle pump system of FIG. 1 according to embodiments of the present disclosure.

FIG. 5 illustrates a close-up side view of the shuttle pump 106. As shown, the shuttle pump 106 can include the pumping piston 108 coupled to the piston grip 110. As indicated, the shuttle pump 106 is shown in a simplified manner. In general, the shuttle pump 106 can be coupled to a reservoir of liquid that can be drawn in to the pumping piston 108 and then expelled out from the pumping piston 108 before the pumping piston 108 is reloaded with the liquid. In various embodiments, the system 100 can be a component of the drug delivery system such that liquid expelled from the pumping piston 108 can be provide to a user or patient of the drug delivery system.

Figure 6:
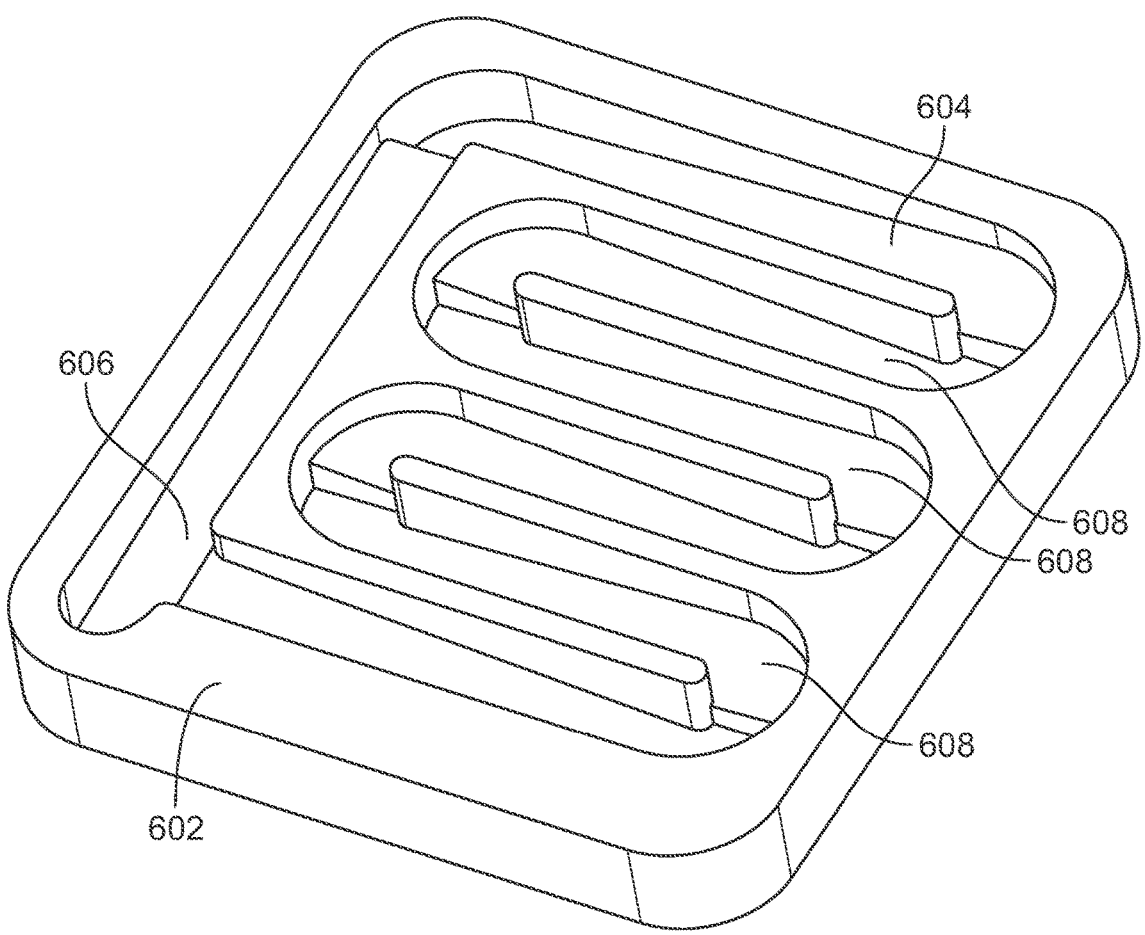
FIG. 6 illustrates a first alternative cam block that can be used with the multiple pulse shuttle pump system of FIG. 1 according to embodiments of the present disclosure.

FIG. 6 illustrates a first alternative cam block (or movement guide) 602. The cam block 602 includes a pathway or path 604 inset or formed into the cam block 602. The cam block 602 can be used as an alternative to the cam block 104. As shown, the cam block 602 can include a first section 606 that extends or runs along a first axis and multiple second sections 608 that each extend or run along a second axis extending perpendicular to the first axis. For purposes of reference, the first axis can be considered a y-axis and the second axis can be considered to be an x-axis. Accordingly, the first section 606 is oriented along the y-axis and the second sections 608 are oriented along the x-axis. The cam block 602 can be made smaller along the x-axis based on the arrangement/orientation of the sections 606 and 608, for example, relative to the cam block 104, thereby allowing the system that includes the cam block 602 to be smaller and more compact. In an embodiment, the section 606 can be traversed by the pin 122 (not shown in FIG. 6) when the pumping piston 108 is to draw in more fluid from the coupled reservoir and the sections 608 can be traversed by the pin 122 when the pumping piston 108 delivers the drawn in fluid over multiple pulses to the user (e.g., expels the drawn in fluid).

Figure 7:
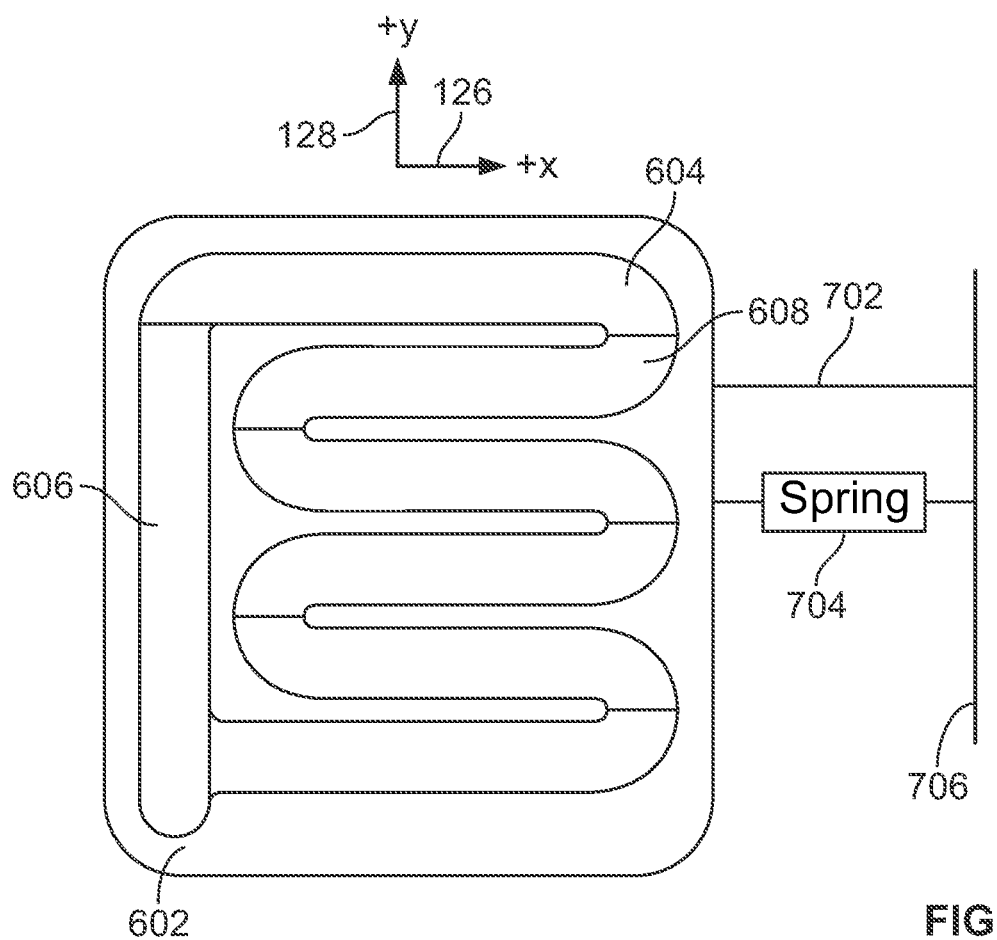
FIG. 7 illustrates an overhead view of the cam block of FIG. 6 according to embodiments of the present disclosure.

FIG. 7 illustrates an overhead view of the cam block 602. As shown in FIG. 7, the cam block 602 can be used in conjunction with a second SMA wire 702 and a third spring 704 (relative to the SMA wire 102 and the first and second springs 112 and 114). Since the sections 608 are oriented entirely along the x-axis 126, the SMA wire 702 and the spring 704 can be used to facilitate actuation of the cam block 602. In an embodiment, the SMA wire 702 can pull on the cam block 602 in a first direction (e.g., a positive x direction relative to the x-axis 126) for each pulse and the spring 704 can push the cam block 602 back in a second opposite direction (e.g., a negative x-direction). The SMA wire 120 can pull on the pumping piston 108 (both not shown in FIG. 7 for simplicity) each time the pumping piston 108 is to draw in fluid from the coupled reservoir (or to reset the system).

Figure 8:
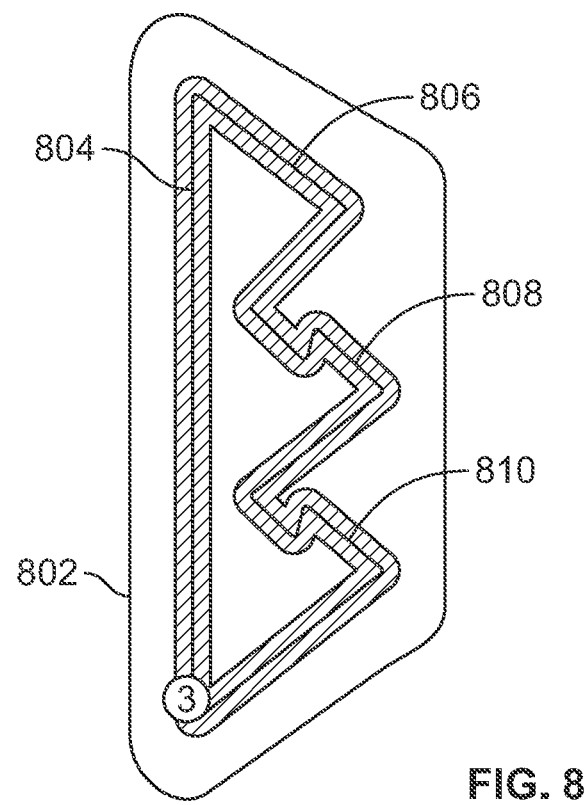
FIG. 8 illustrates a second alternative cam block that can be used with the multiple pulse shuttle pump system of FIG. 1 according to embodiments of the present disclosure.

FIG. 8 illustrates a second alternative cam block (or movement guide) 802. The cam block 802 includes a pathway or path 804 inset or formed into the cam block 802. The cam block 802 can be used as an alternative to the cam block 104. As shown, the cam block 602 can include a first section 806, a second section 808, and a third section 810. The pin 122 (not shown) can traverse the sections 806, 808, and 810 to cause the pumping piston 108 to draw in fluid from the coupled reservoir and to then expel the drawn in fluid form the pumping piston 108. In an embodiment, to cause the pin 122 to traverse the path 804, the cam block 802 can be used with one or more additional SMA wires or springs. As shown, in an embodiment, the cam block 802 can be made smaller and more compact that the cam blocks 104 and 602, thereby allowing a drug delivery device that uses the cam block 802 to made smaller and more compact.

Figure 9:
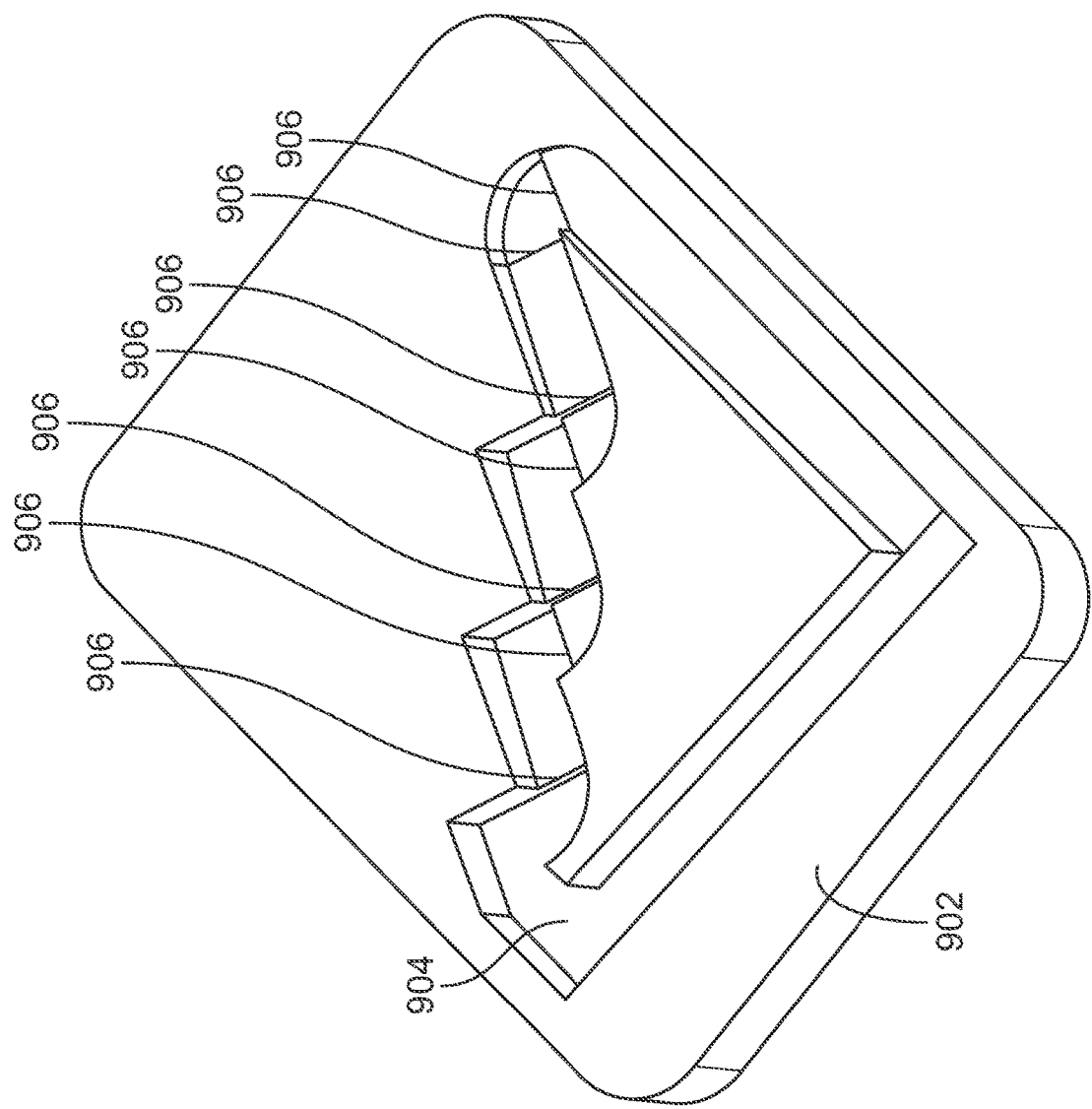
FIG. 9 illustrates a third alternative cam block that can be used with the multiple pulse shuttle pump system of FIG. 1 according to embodiments of the present disclosure.

FIG. 9 illustrates a third alternative cam block (or movement guide) 902. The cam block 902 includes a pathway or path 904 inset or formed into the cam block 902. The cam block 902 can be used as an alternative to the cam block 104. The path 904 can include multiple different sections. Further, the cam block 902 can include multiple drop offs or ledges 906 positioned between (e.g., at the interfaces between) adjacent sections of the path 904 as shown.

Figure 10:
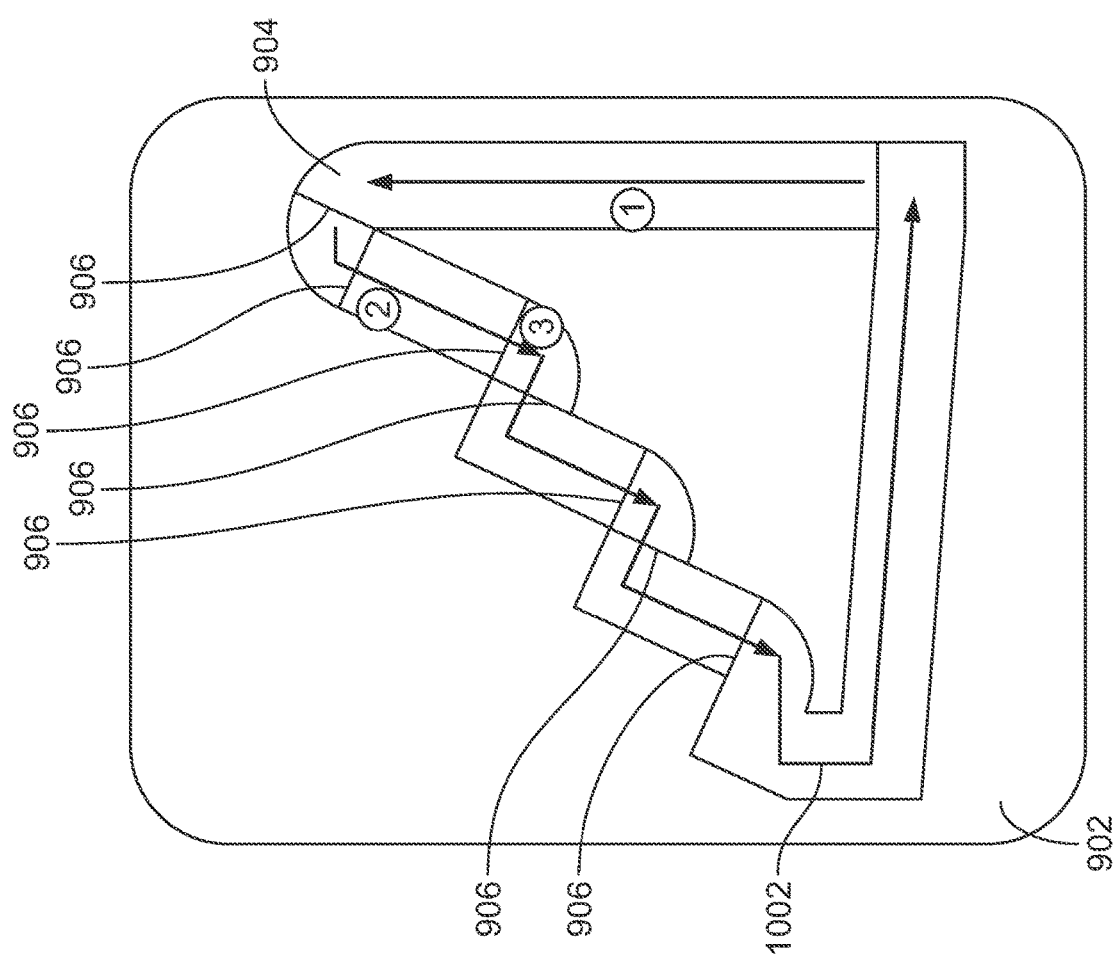
FIG. 10 illustrates an overhead view of the cam block of FIG. 9 according to embodiments of the present disclosure.

FIG. 10 illustrates an overhead view of the cam block 902. As shown, the cam block 902 includes a route 1002 of the pin 122 (e.g., as indicated by the sequence of arrows collectively referenced by the route label 1002). In various embodiments, the SMA wire 120 can be sequentially activated and deactivated to cause the pin 122, in conjunction with associated movement of the cam block 902, to traverse the route 1002 of the path 904. In an embodiment, exemplary positions of the pin 122 are shown as labeled positioned "1", "2" and "3". At "1", the pin 122 can be pulled up a ramp or incline based on activation of the SMA wire 120. At "2", the pin 122 can fall over the drop off 906 and can be restricted from moving backwards. The pin 122 reaching position "2" can correspond to a single pulse of the system. At "3", the pin 122 can fall over the next drop off 906 and can move into the next slot or portion of the path 904 by actuation of the SMA wire 120. This process can be repeated to cause the pin 122 to traverse the route 1002 along the path 904.

Figure 11:
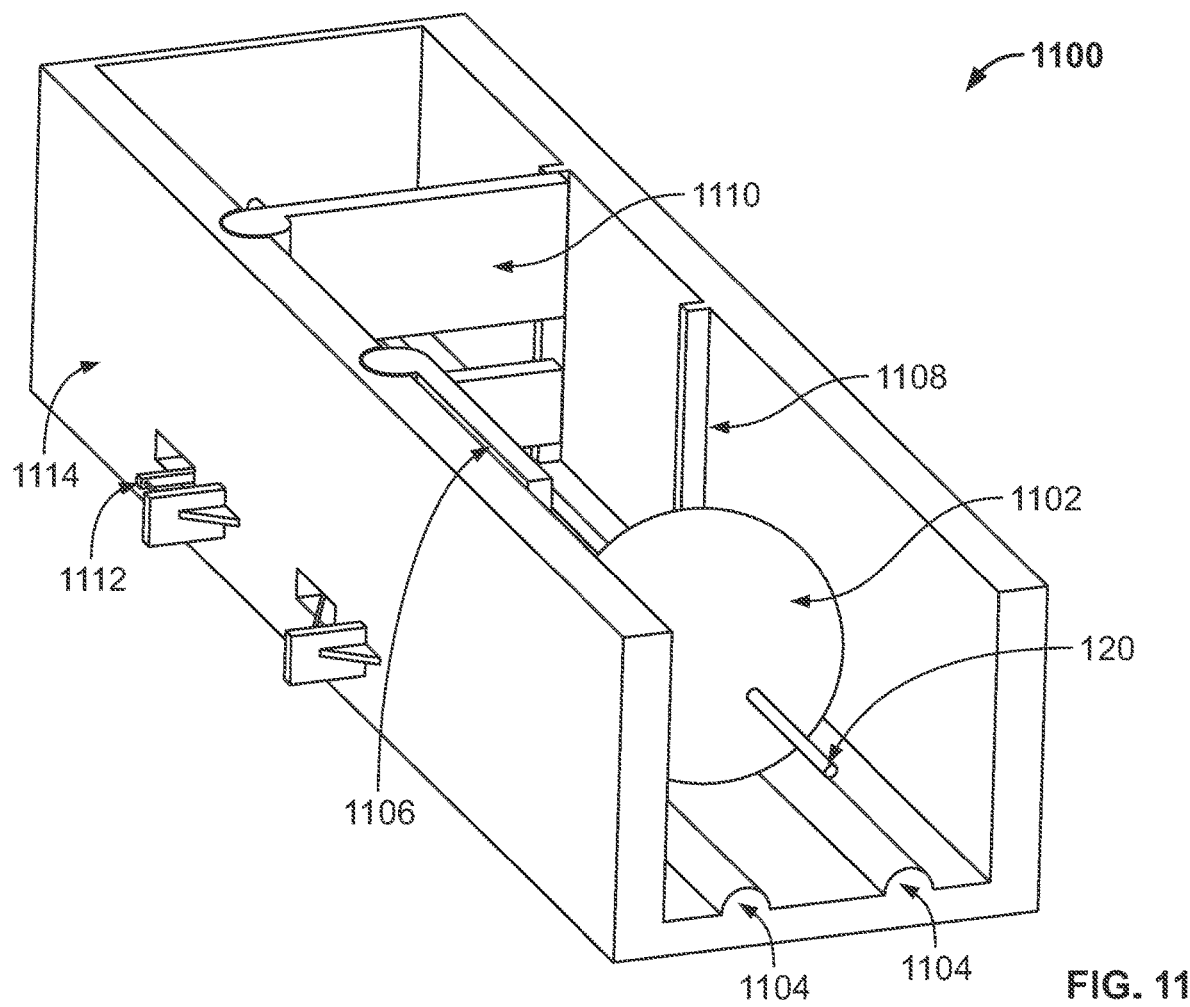
FIG. 11 illustrates a second multiple pulse shuttle pump system with a wire according to embodiments of the present disclosure.

FIG. 11 illustrates a second exemplary embodiment of a multiple pulse shuttle pump system (hereinafter "system") 1100. The system 1100 can include the SMA wire 120, a housing 1114, a ball bearing 1102, a track 1104, a first gate 1106, a first backstop 1108, a second gate 1110, and a gate actuator 1112. The SMA wire 120 can be attached to a pump, for example, the pumping piston 108. The ball bearing 1102 can be rigidly connected to the SMA wire 120. The track 1104 can provide a guide for the ball bearing 1102. In particular, the ball bearing 1102 can move back and forth along the track 1104 with the housing 1114 in accordance with the linear motion of the piston pump 108, as determined by actuation of the SMA wire 120.

The first gate 1106 is shown in an open position, allowing movement of the ball bearing 1102 beyond the first gate 1106. The gate backstop 1108 can block the first gate 1106 from swinging too far when in a closed position. The second gate 1110 is shown in a closed position and so can restrict further movement of the ball bearing 1102 in a direction past the second gate 1110. By restricting movement of the ball bearing 1102, the second gate 1110 (or any closed gate) can interrupt operation of the pumping piston 108, for example, by interrupting a filling process of the pumping piston 108 at predetermined volume intervals. A gate actuator 1112 can control motion of the second gate 1110. Each gate can be controlled by a corresponding gate actuator to be in an open or a closed position.

The system 1100 is not limited to the number of gates shown as any number of gates can be used with the system 1100. Further, each gate can be accompanied by a gate backstop to set a closed position for a corresponding gate. The SMA wire 120, when activated, can pull on the ball bearing 1102 in a direction from the open gate 1106 to the closed gate 1110 (e.g., towards the closed end of the housing 1114). When deactivated, the ball bearing 1102 can be pulled in the opposite direction. For each direction, movement of the ball bearing 1102 can be regulated by the gates 1106 and 1110, to control filling of the pumping piston 108 with a fluid and to control expelling the fluid from the pumping piston 108. In particular, the gates 1106 and 1110 can control the movement of the ball bearing 1102 and corresponding linear motion of the pumping piston 108 at fixed predetermined intervals or positions based on pulses of the SMA wire 120.

Figure 12:
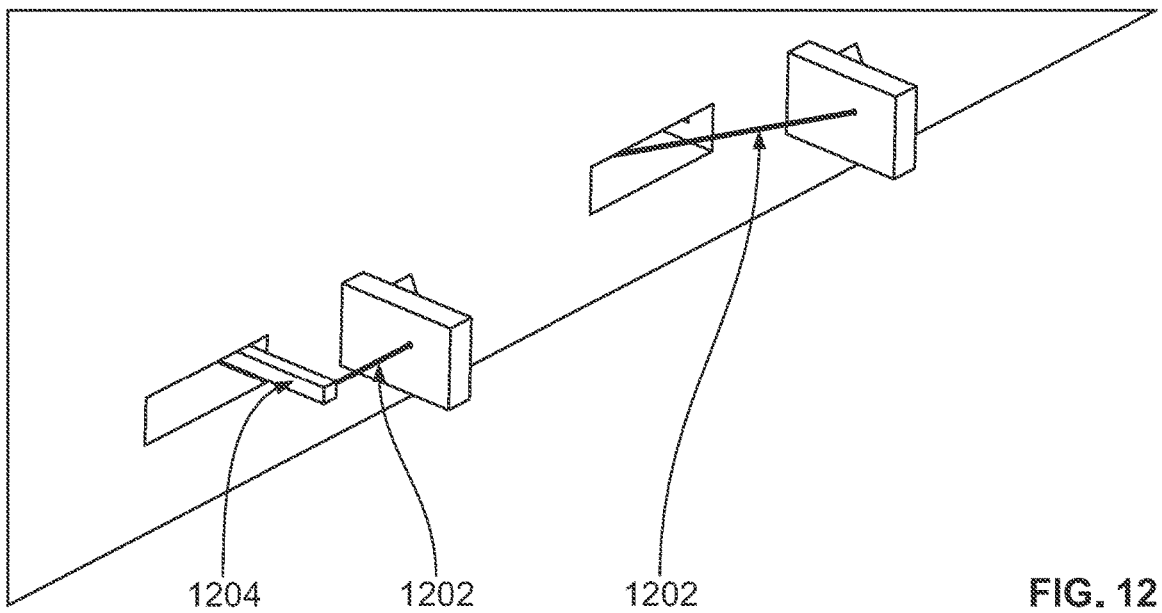
FIG. 12 illustrates a first close-up view of a portion of the multiple pulse shuttle pump system of FIG. 11 according to embodiments of the present disclosure.

FIG. 12 illustrates a first close-up view of a portion of the system 1100. As shown, SMA wires 1202 can be used as part of the gate actuators. For example, a lever 1204 coupled to a gate can be pulled by one of the SMA wires 1202 when activated, to open or close the corresponding gate. In this way, the state of each gate can be controlled.

Figure 13:
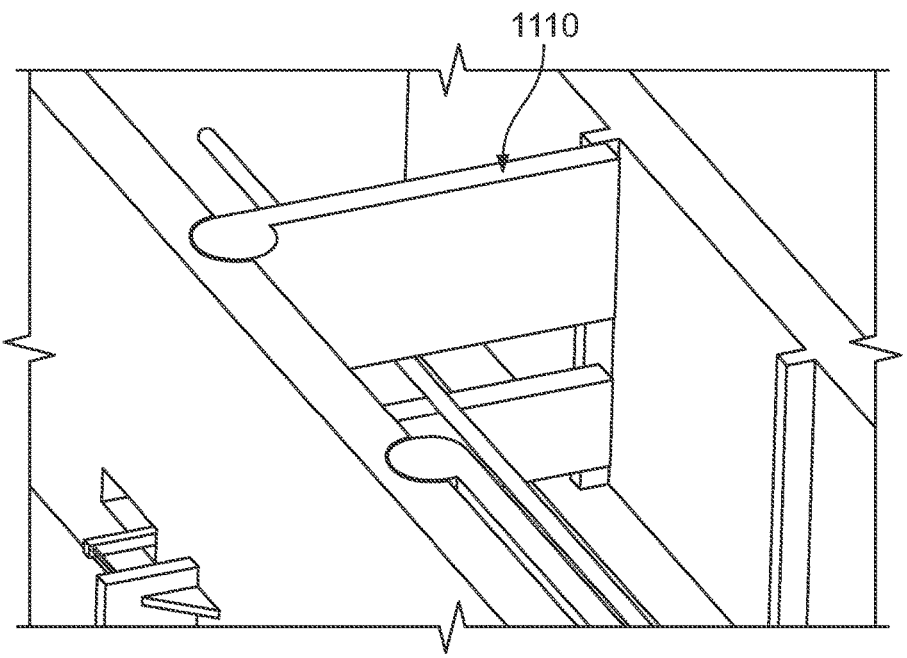
FIG. 13 illustrates a second close-up view of a portion of the multiple pulse shuttle pump system of FIG. 11 according to embodiments of the present disclosure

FIG. 13 illustrates a second close-up view of a portion of the system 1100. In an embodiment, the gate 1110, the corresponding backstop, and the ball bearing 1102 (not shown) can be used to operate as an electrical contact sensor. In this way, a position of the ball bearing 1102 may be determined during operation of the system 1100 so as to determine when to activate/deactivate the SMA wire 120 and or the SMA wires 1202 for controlling respective gates.

Figure 14:
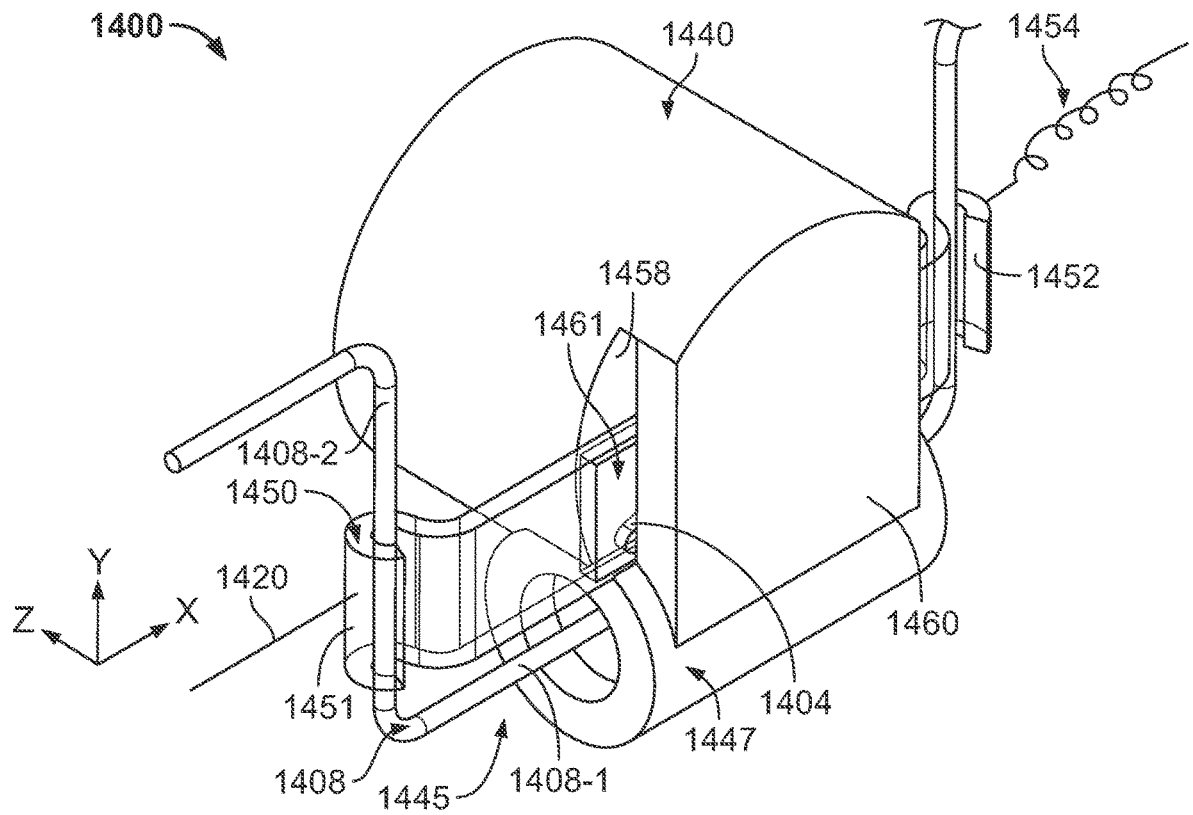
FIG. 14 illustrates a portion of a shuttle pump system according to embodiments of the present disclosure.

FIG. 14 illustrates a portion of a shuttle pump system (hereinafter "system") 1400 according to embodiments of the present disclosure. As shown, the system 1400 includes, a pump chamber 1440, which may be a reservoir for storing a fluid (e.g., insulin). The pump chamber 1440 may be integrally formed or coupled to a valve assembly 1445 including a valve 1447. As will be described in greater detail herein, the valve 1447 is operable with the pump chamber 1440 to cycle through two open states for filling and dispensing the fluid from the pump chamber 1440. The system 1400 may further include a wire 1420 coupled to a valve shaft 1408, wherein the wire 1420 may move the valve shaft 1408 when the wire 1420 is pulled (e.g., in a negative x-direction). In some embodiments, the wire 1420 is a shape memory alloy (SMA) wire.

The system 100 may further include a cam bracket 1450 of the system 1400. As shown, the cam bracket 1450 may couple together the wire 1420 and the valve shaft 1408. In some embodiments, the cam bracket 1450 includes a pair of curled ends 1451, 1452 engaged with the valve shaft 1408. As shown, the valve shaft 1408 may include a first section 1408-1 extending perpendicular to a second section 1408-2. For example, the first section 1408-1 may generally extend parallel to the x-direction, and the second section 1408-2 may generally extend parallel to the y-direction. In some embodiments, curled end 1451 may be directly coupled to the wire 1420, and curled end 1452 may be coupled to one or more springs 1454. During operation, the spring 1454 may bias the cam bracket 1450 along the positive x-direction, while the wire 1420 may bias the cam bracket 1450 along the negative x-direction when pulled. To maintain alignment thereof, the cam bracket 1450 may be disposed between an exterior surface 1458 of the pump chamber 1440 and a bracket wall 1460. In some embodiments, the bracket wall 1460 is coupled to both the valve 1447 and the pump chamber 1440.

Figure 15A:
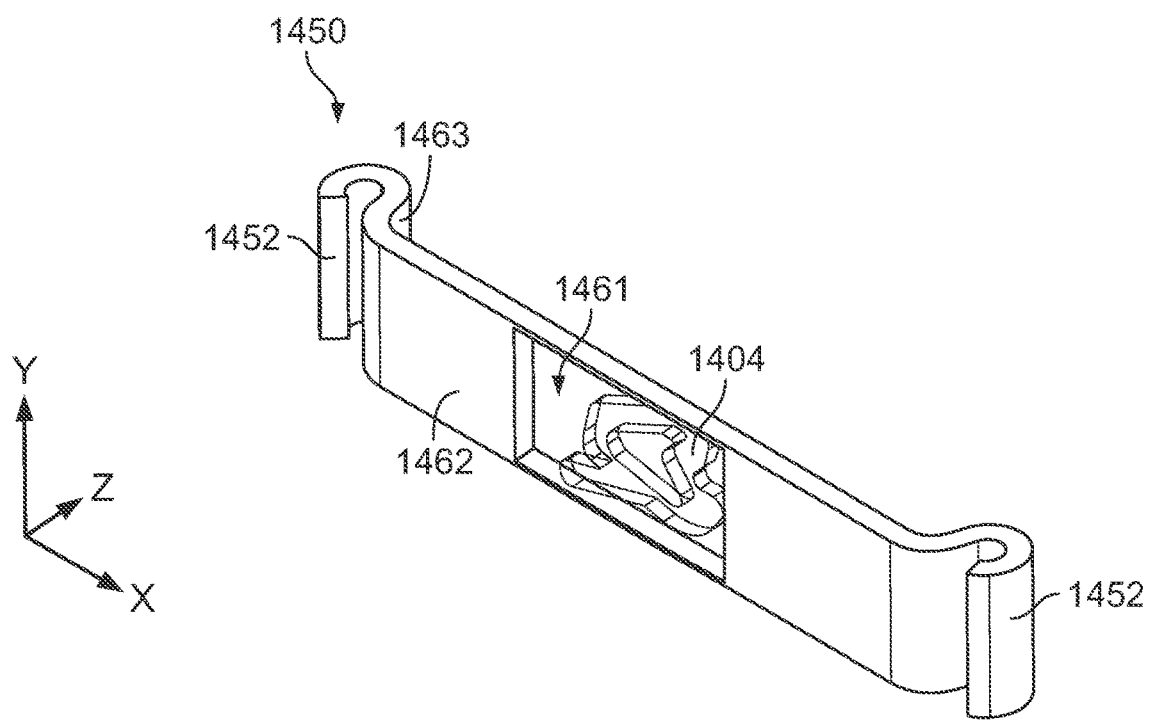
FIG. 15A illustrates a cam bracket of the shuttle pump system of FIG. 14 according to embodiments of the present disclosure.

As shown in FIG. 14 and FIG. 15A, the cam bracket 1450 may further include a cam 1461 having an asymmetrical inset pathway 1404, wherein a pin (not shown) extending from the exterior surface 1458 of the pump chamber 1440 is configured to traverse the inset pathway 1404 during operation. In some embodiments, the inset pathway 1404 may extend fully or partially between a first main side 1462 and a second main side 1463 of the cam bracket 1450. In an alternative embodiment, the cam 1461 and the inset pathway 1404 may be provided along the exterior surface 1458 of the pump chamber 1440, while the pin is provided along the second main side 1462 of the cam bracket 1450.

Figure 15B:
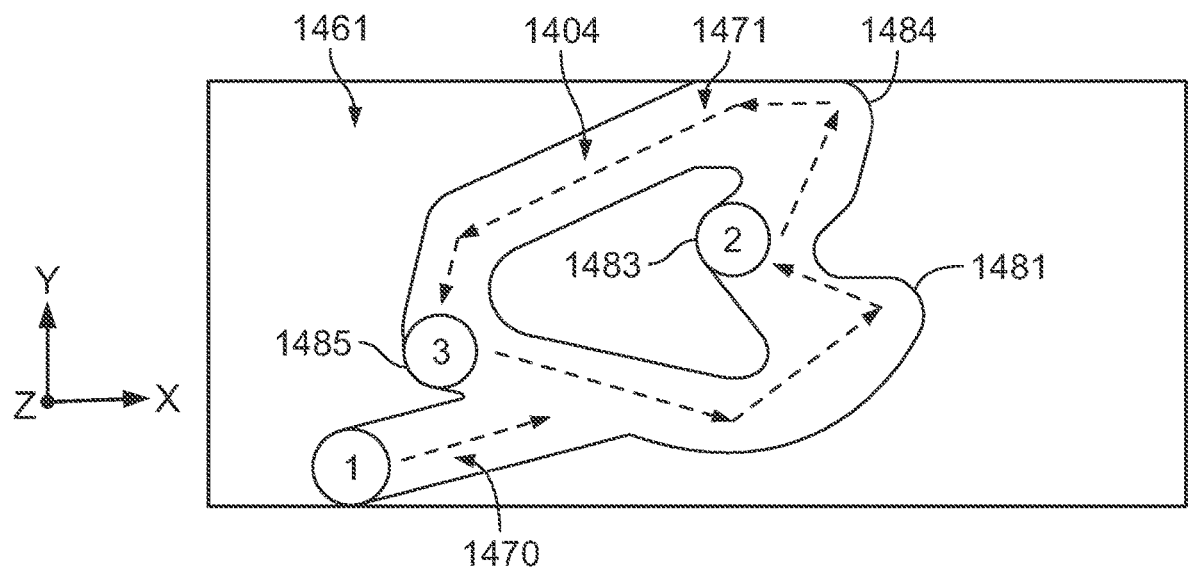
FIG. 15B illustrates a cam and inset pathway of the cam bracket of FIG. 15A according to embodiments of the present disclosure.

FIG. 15B illustrates the cam 1461 and inset pathway 1404 in greater detail. As shown, the inset pathway 1404 may include a first branch 1470 connected to a primary loop 1471. Circles (1), (2), and (3) in FIG. 15B represent the three primary states of the valve 1447. For example, state (1) corresponds to a first hold state in which the valve 1447 is closed, state (2) corresponds to a state in which the valve 1447 is open and filling, and state (3) corresponds to state in which the valve 1447 is open and dispensing. In some embodiments, state (1) may only occur once in life cycle of the valve assembly 1145, for example, during manufacturing. After the pin enters the primary loop 1471, the pin position will alternate between states (2) and (3). In some embodiments, the bracket 1450 is configured to move only in the x-direction and the y-direction.

Turning now to FIGS. 16A-16E, with reference to the inset pathway 1404 of FIG. 15B, further operation of the system 1400 according to embodiments of the present disclosure will be described in greater detail. As demonstrated in FIG. 16A, the valve assembly 1445 may be in an initial closed state, such as state (1) shown in FIG. 15B. A pin 1475 may be positioned within the first branch 1470 of the inset pathway 1404. As shown, all of openings 1476, 1477, and 1478, which are formed through the valve shaft 1408, are covered by a first inner cylinder 1479 of the valve 1447. With the wire 1420 is in a relaxed state, the springs 1454 pull the bracket 1450 and the valve shaft 1408 in the positive x-direction (i.e., towards the right).

As demonstrated in FIG. 16B, the wire 1420 is then pulled in the negative x-direction (i.e., towards the left), causing the bracket 1450 and the valve shaft 1408 to also move in the negative x-direction. The pin 1475 may accordingly enter and engage a first notch 1481 of the inset pathway 1404. The openings 1476, 1477, and 1478 may now be covered by a second inner cylinder 1480 of the valve 1447. The first inner cylinder 1479 and the second inner cylinder 1480 may be separated from one another by a gap 1482. As shown by distance 'D1', the pin 1475 moving from the first branch 1470 to the first notch 1481 represents a maximum stroke of the wire 1420.

Figure 16C:
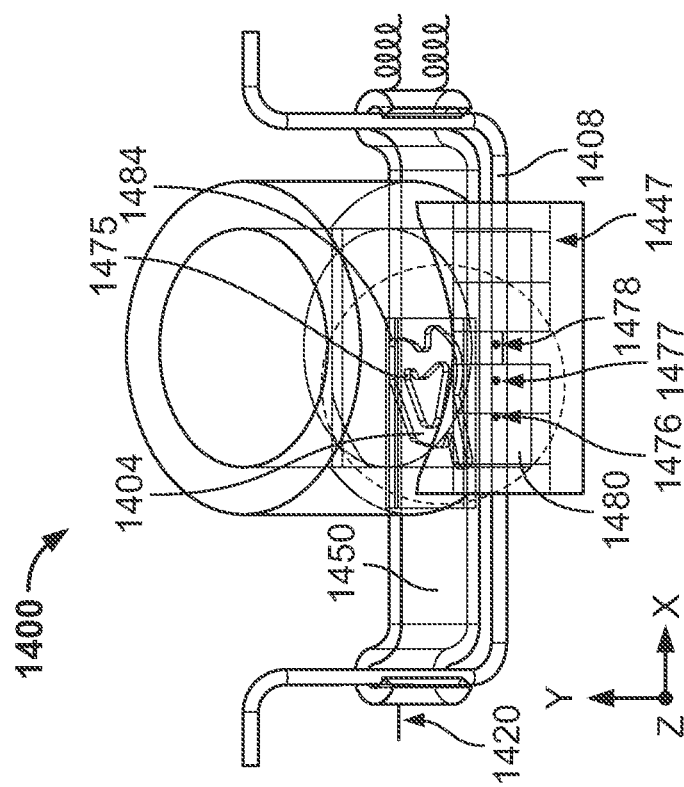

As demonstrated in FIG. 16C, tension on the wire 1420 may be released or relaxed, causing the bracket 1450 to move generally in the positive x-direction and negative y-direction, and the valve shaft 1408 to move in the positive x-direction due to the spring force of the springs 1454. The pin 1475 may accordingly enter and engage a second notch 1483 of the inset pathway 1404. The openings 1476 and 1477 remain covered by the second inner cylinder 1480 of the valve 1447, but opening 1478 is now exposed within the gap 1482. In this position of the valve shaft 1408, the valve assembly 1445 may be in a first open state, such as state (2) shown in FIG. 15B, which allows the pump chamber 1440 to be filled.

Figure 16D:
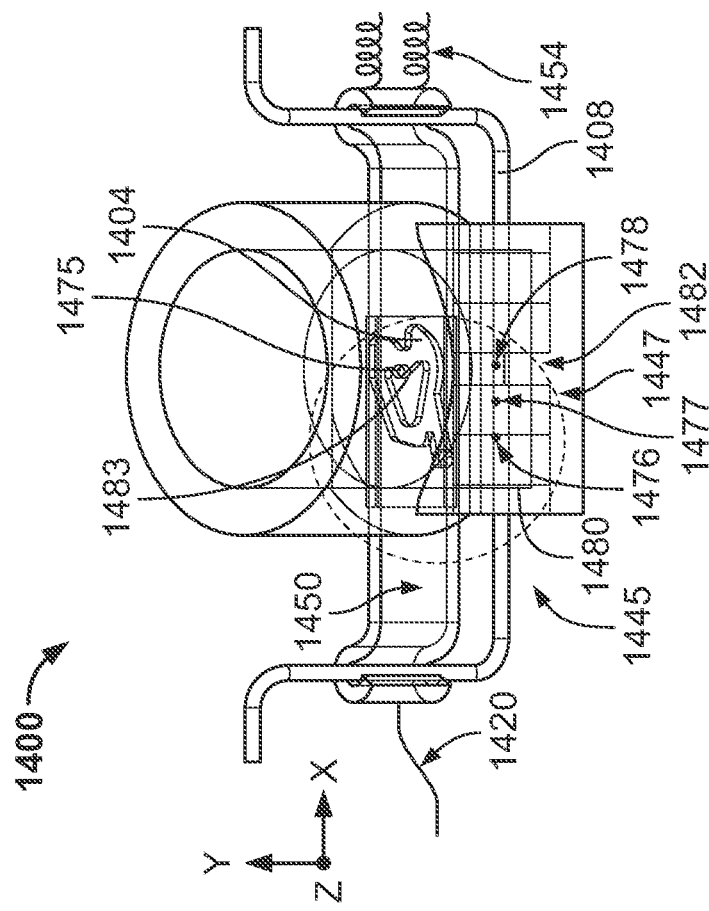

As demonstrated in FIG. 16D, tension on the wire 1420 may be increased, causing the bracket 1450 to move generally in the negative x-direction and negative y-direction. The pin 1475 may accordingly enter and engage a third notch 1484 of the inset pathway 1404. The valve shaft 1408 moving in the negative x-direction causes openings 1476, 1477, and 1478 of the valve shaft 1408 to again be covered by the second inner cylinder 1480 of the valve 1447.

Figure 16E:
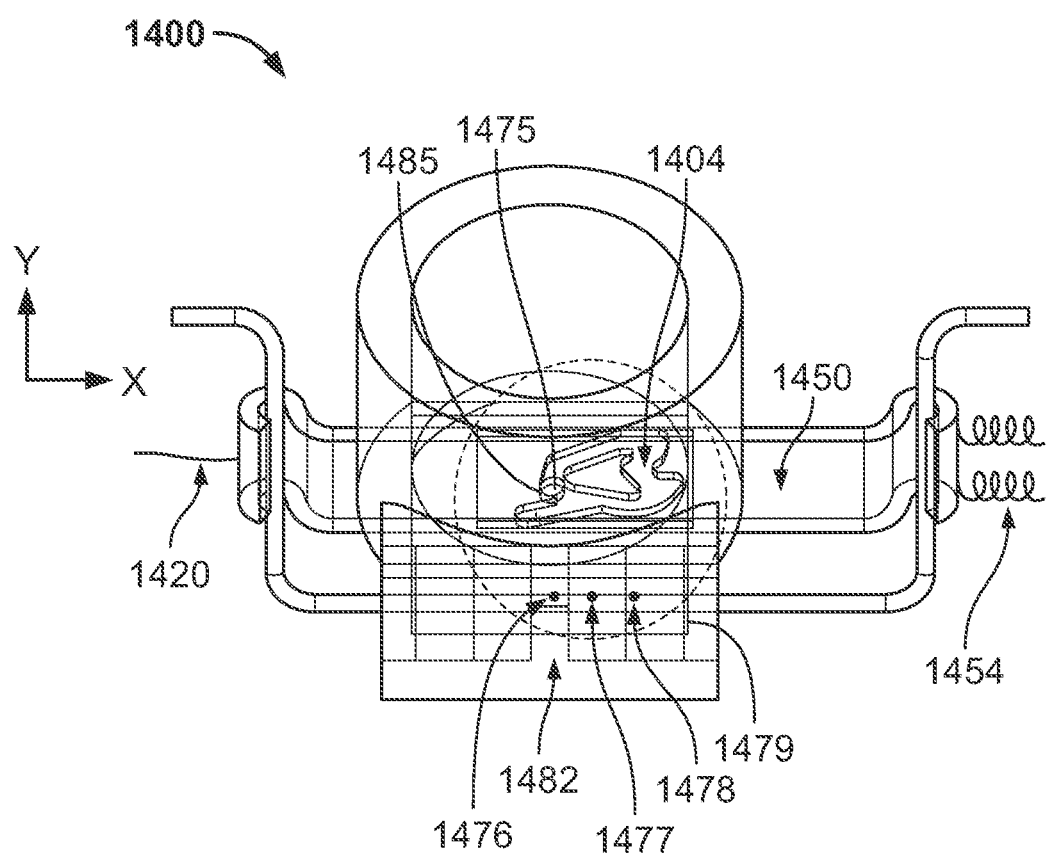

As demonstrated in FIG. 16E, tension on the wire 1420 may be released or relaxed, causing the bracket 1450 to move generally in the positive x-direction and positive y-direction, and the valve shaft 1408 to move in the positive x-direction due to the spring force of the springs 1454. The pin 1475 may accordingly enter and engage a fourth notch 1485 of the inset pathway 1404. The openings 1477 and 1478 become covered by the first inner cylinder 1479 of the valve 1447, but opening 1476 is now exposed within the gap 1482. In this position of the valve shaft 1408, the valve assembly 1445 may be in a second open state, such as state (3) shown in FIG. 15B, which allows the pump chamber 1440 to dispense a liquid drug (e.g., insulin) therefrom.

Figure 17A:
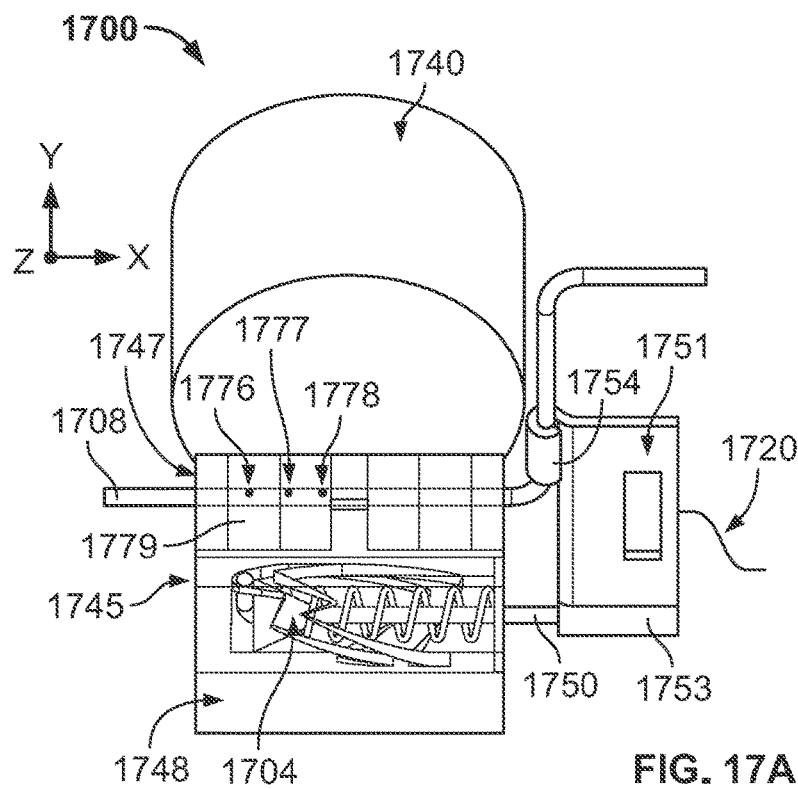
FIG. 17A illustrates a portion of a shuttle pump system according to embodiments of the present disclosure.
Figure 17B:
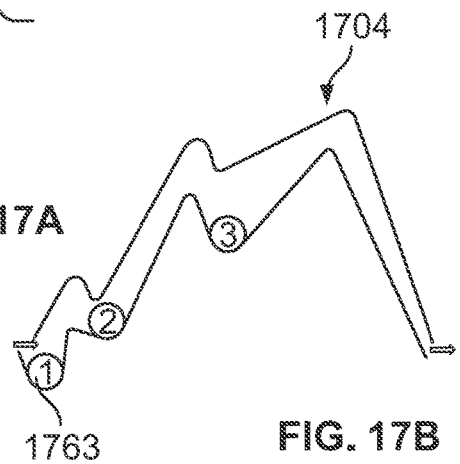
FIG. 17B illustrates an inset pathway of the shuttle pump system of FIG. 17A according to embodiments of the present disclosure.
Figure 17C:
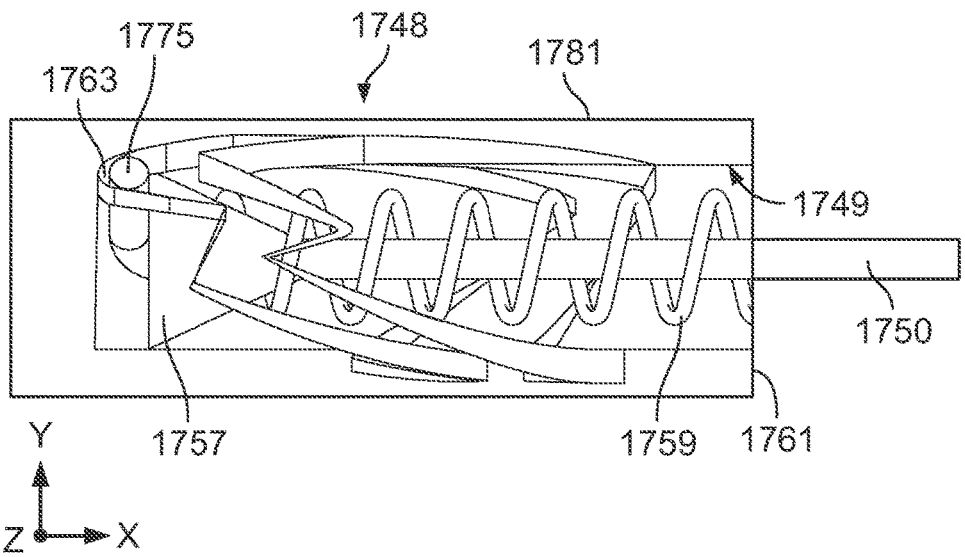
FIG. 17C illustrates a chamber of a valve assembly of the shuttle pump system of FIG. 17A according to embodiments of the present disclosure.

Turning now to FIGS. 17A-17C, a portion of a shuttle pump system (hereinafter "system") 1700 according to embodiments of the present disclosure will be described. As shown, the system 1700 includes a pump chamber 1740, which may be a reservoir for storing a fluid (e.g., insulin). The pump chamber 1740 may be integrally formed or coupled to a valve assembly 1745 including a valve 1747. The valve 1447 is operable with the pump chamber 1740 to cycle through two open states for filling and dispensing the fluid from the pump chamber 1740. The system 1700 may further include a wire 1720 coupled to a valve shaft 1708, wherein the wire 1720 may move the valve shaft 1708 when the wire 1720 is pulled (e.g., in a positive x-direction). In some embodiments, the wire 1720 is a shape memory alloy (SMA) wire.

As further shown, the valve assembly 1745 may include a chamber 1748 adjacent the valve 1747, the chamber 1748 including an asymmetrical inset pathway 1704 along an interior surface thereof. The valve assembly 1745 may further include a second shaft 1750 extending within the chamber 1745, wherein a pin 1775 extends from an end of the second shaft 1750, and wherein movement of the pin 1775 within the inset pathway 1704 causes the chamber 1748 to rotate about the second shaft 1750. As shown, the second shaft 1750 may be configured as a bent needle, wherein the pin 1775 generally extends perpendicular to the remainder of the second shaft 1750. The inset pathway 1704 wraps around an interior of the chamber 1748, restricting the pin 1775 to follow a desired path. Numbers (1), (2), and (3) along the inset pathway 1704 in FIG. 17B correspond to different hold positions or states of the pin 1775 and the second shaft 1750. In some embodiments, the inset pathway 1704 runs within an inner bore 1749 of the chamber 1748. However, the inset pathway 1704 may not extend completely through a wall of chamber 1748, thus providing the chamber 1748 with a solid, cylindrical exterior surface 1781.

The valve assembly 1745 may include a bracket 1751 coupling together the valve shaft 1708 and the second shaft 1750. Although non-limiting, the bracket 1751 may be configured as plate including a cylindrical receptacle 1753 receiving the second shaft 1750 and a curled arm 1754 receiving the valve shaft 1708. As shown, the wire 1720 may be directly coupled to the bracket 1751.

As best shown in FIG. 17C, in some embodiments, the valve assembly 1745 may further include a stopper 1757 coupled to the second shaft 1750, and a chamber spring 1759 in abutment with the stopper 1757. As shown, the chamber spring 1759 may extend around the second shaft 1750, biasing the stopper 1757 and the pin 1775 in the negative x-direction within the chamber 1748. When the wire 1720 is pulled in the x-direction, the chamber spring 1759 is compressed against an end wall 1761 of the chamber 1748.

In the initial state shown in FIGS. 17A-17C, the chamber spring 1759 pushes the stopper 1757 and the pin 1775 into a first notch 1763 of the inset pathway 1704. In this position of the second shaft 1750, the valve assembly 1745 may be in a closed state, such as state (1) shown in FIG. 17B. As a result, all of openings 1776, 1777, and 1778 (FIG. 17A), which are formed through the valve shaft 1708, may be covered by a first inner cylinder 1779 of the valve 1747. With the wire 1720 in a relaxed state, the chamber spring 1759 pushes the valve shaft 1708 and the second shaft 1750 in the negative x-direction (i.e., towards the left).

Figure 18A:
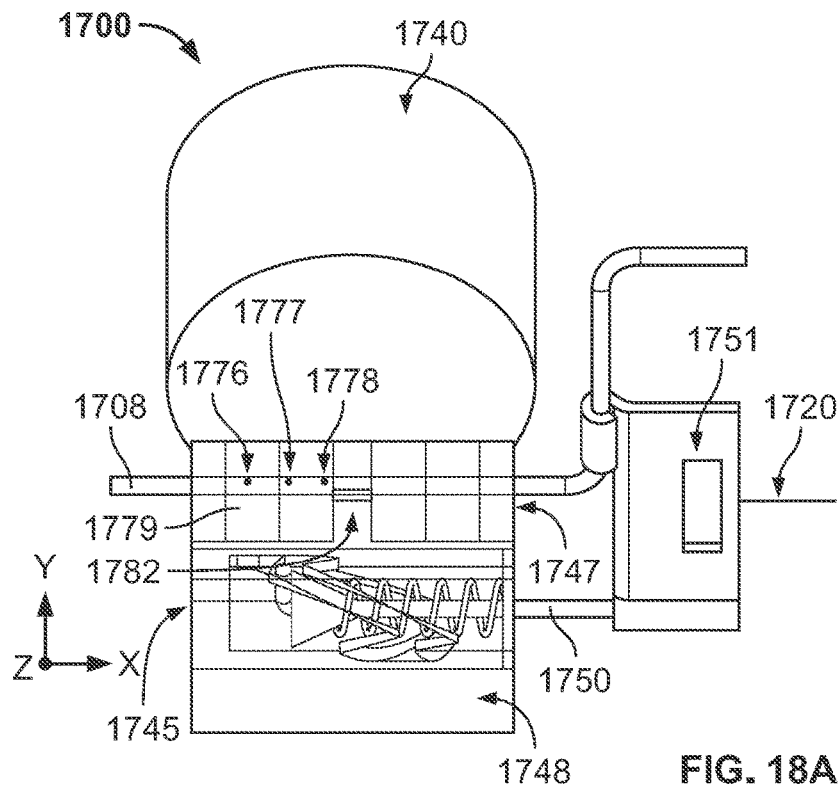
FIG. 18A illustrates the portion of a shuttle pump system according to embodiments of the present disclosure.
Figure 18B:
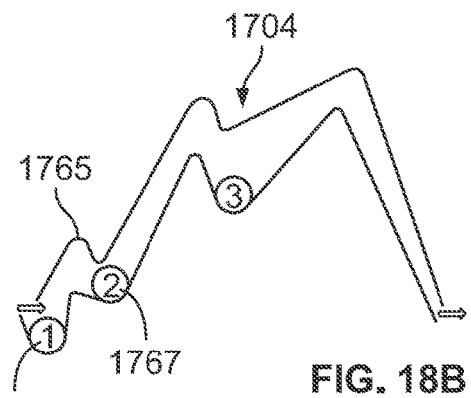
FIG. 18B illustrates the inset pathway of the shuttle pump system of FIG. 18A according to embodiments of the present disclosure.
Figure 18C:
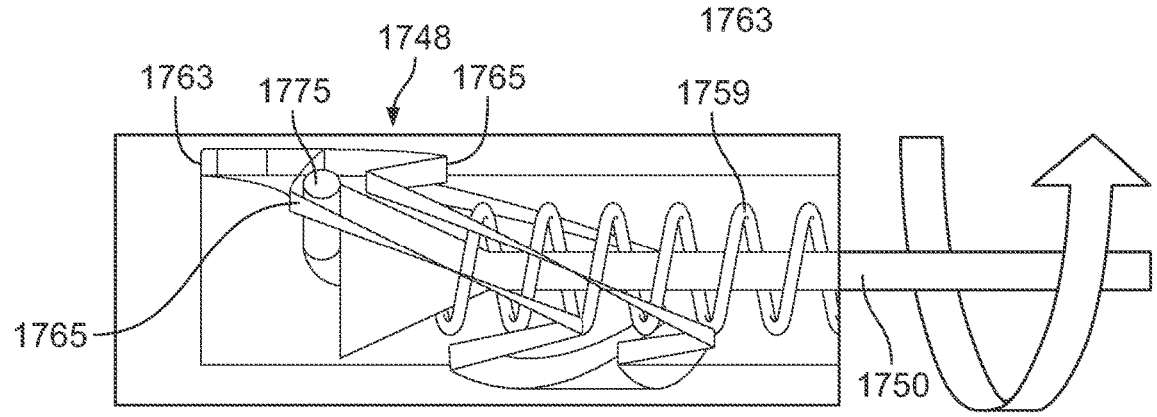
FIG. 18C illustrates the chamber of the valve assembly of the shuttle pump system of FIG. 18A according to embodiments of the present disclosure.

Next, as demonstrated in FIGS. 18A-18C, the wire 1720 is pulled in the positive x-direction (i.e., towards the right), causing the bracket 1751, the valve shaft 1708, and the second shaft 1750 to also move in the positive x-direction. As the wire 1720 is pulled, the chamber 1748 may rotate relative to the pin 1775, causing the pin 1775 to initially enter and engage a second notch 1765 of the inset pathway 1704. The wire 1720 may then be released or relaxed, causing the bracket 1751, the valve shaft 1708, and the second shaft 1750 to move in the negative x-direction in response to a spring force from the chamber spring 1759. The pin 1775 may then enter and engage a third notch 1767 while the wire 1720 is relaxed. As shown in FIG. 18A, openings 1776 and 1777 remain covered by the first inner cylinder 1779 of the valve 1747. However, opening 1778 is now exposed within a gap 1782. In this position of the valve shaft 1708, the valve assembly 1745 may be in a first open state, such as state (2) shown in FIG. 18B, which connects the valve 1747 to the pump chamber 1740 for filling.

Figure 19A:
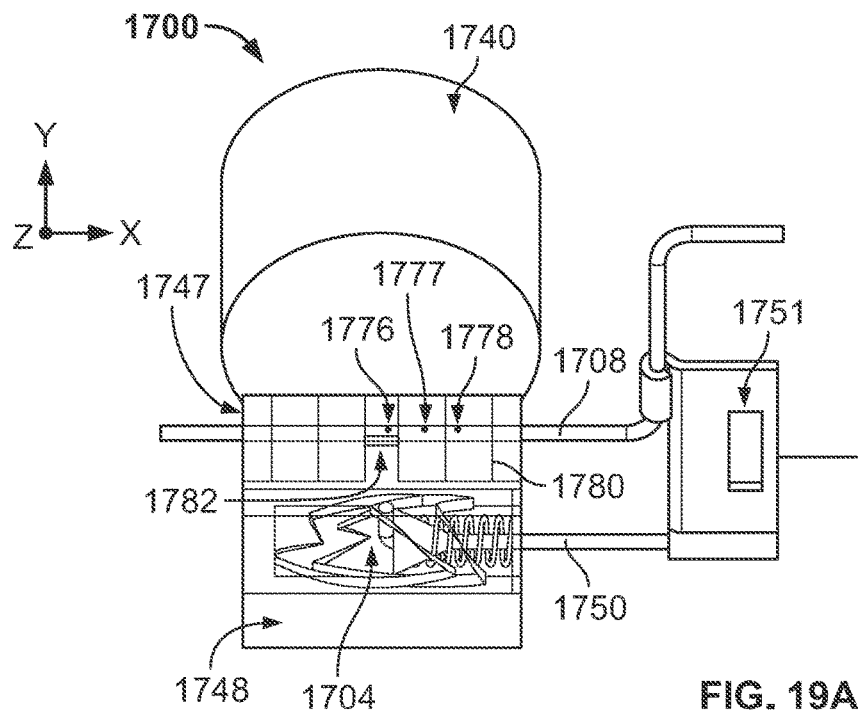
FIG. 19A illustrates the portion of a shuttle pump system according to embodiments of the present disclosure.
Figure 19B:
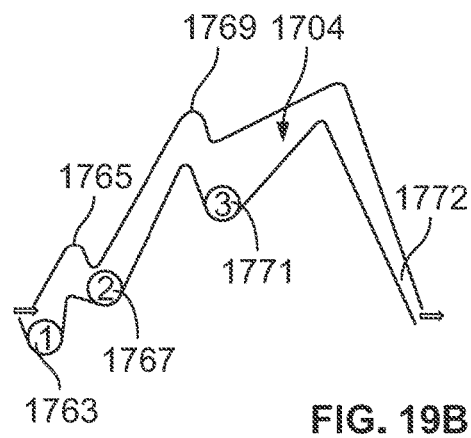
FIG. 19B illustrates the inset pathway of the shuttle pump system of FIG. 18A according to embodiments of the present disclosure.
Figure 19C:
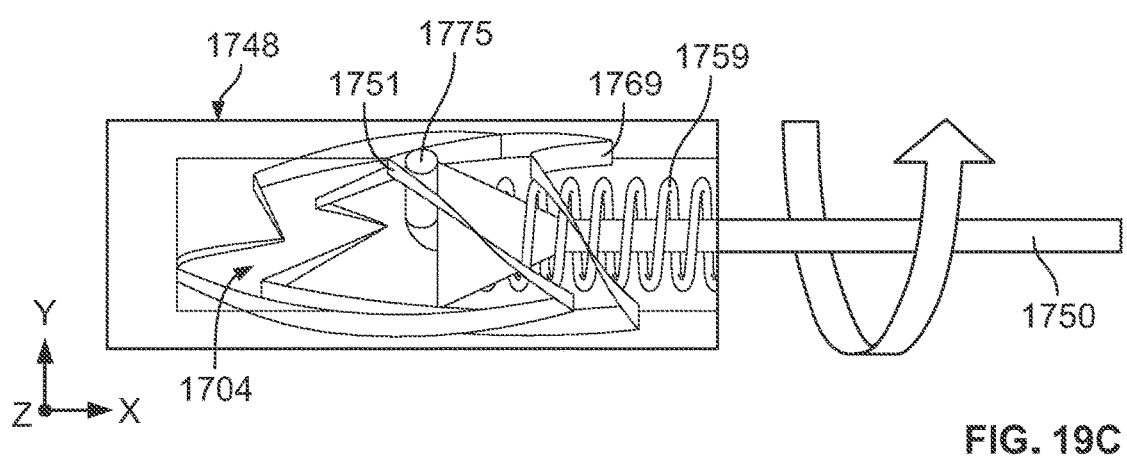
FIG. 19C illustrates the chamber of the valve assembly of the shuttle pump system of FIG. 19A according to embodiments of the present disclosure.

Next, as demonstrated in FIGS. 19A-19C, the wire 1720 is again pulled in the positive x-direction, causing the bracket 1751, the valve shaft 1708, and the second shaft 1750 to also move in the positive x-direction. As the wire 1720 is pulled, the chamber 1748 again rotates until the pin 1775 enters and engages a fourth notch 1769 of the inset pathway 1704. The wire 1720 may then be released or relaxed, causing the bracket 1751, the valve shaft 1708, and the second shaft 1750 to move in the negative x-direction until the pin 1775 enters and engages a fifth notch 1771. As shown in FIG. 19A, openings 1777 and 1778 are now covered by a second inner cylinder 1780 of the valve 1747. However, opening 1776 is exposed within the gap 1782. In this position of the valve shaft 1708, the valve assembly 1745 may be in a second open state, such as state (3) shown in FIG. 19B, which opens the valve 1747 for dispensing the liquid drug to a patient. After the liquid drug has been dispensed, the wire 1720 may again be pulled until the pin 1775 reach an end 1772 of the inset pathway 1704. In some embodiments, the pin 1775 may return along the inset pathway 1704 to the closed state, such as state (1), in which the pin 1775 is engaged with the first notch 1763.

Figure 20:
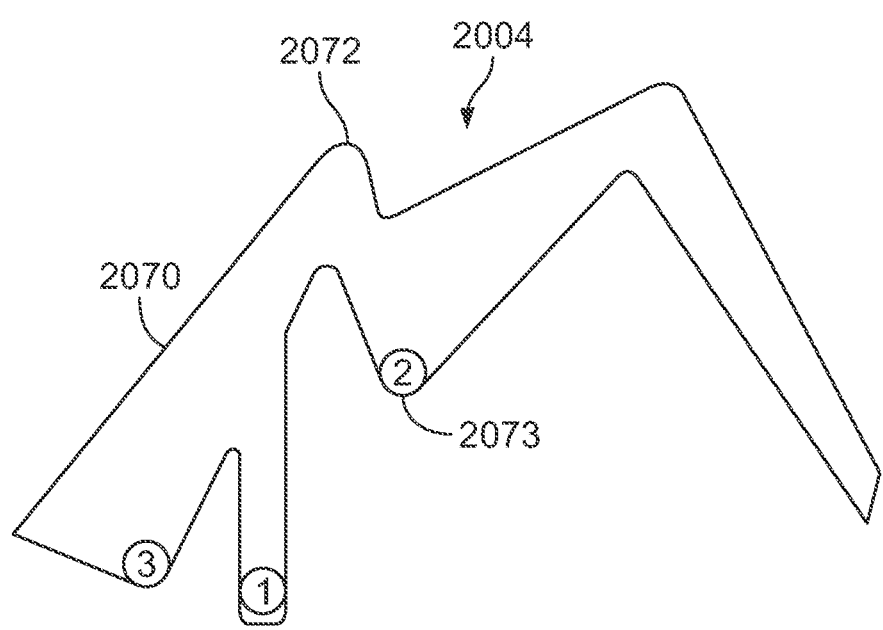
FIG. 20 illustrates an alternative inset pathway according to embodiments of the present disclosure.

FIG. 20 shows an alternative inset pathway 2004 according to embodiments of the present disclosure. Here, the pin (not shown) begins in a closed position or state (1), and then cycles between open states (2) and (3) upon actuation of the wire. Similar to previous embodiments, open state (2) may correspond to a state in which the pump chamber is filled, while open state (3) may correspond to a state in which fluid is dispensed from the pump chamber. In this embodiment, when the shaft is pushed back to state (3) by the spring, the shaft may move along and engage an upper wall 2070 until the shaft reaches a first notch 2072. The inset pathway 2004 is configured to cause the pin to then drop into a second notch 2073, which corresponds to the open state (2).

The foregoing discussion has been presented for purposes of illustration and description and is not intended to limit the disclosure to the form or forms disclosed herein. For example, various features of the disclosure may be grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein.

The phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other.

Furthermore, identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

Furthermore, the terms "substantial" or "substantially," as well as the terms "approximate" or "approximately," can be used interchangeably in some embodiments, and can be described using any relative measures acceptable by one of ordinary skill in the art. For example, these terms can serve as a comparison to a reference parameter, to indicate a deviation capable of providing the intended function. Although non-limiting, the deviation from the reference parameter can be, for example, in an amount of less than 1%, less than 3%, less than 5%, less than 10%, less than 15%, less than 20%, and so on.

Still furthermore, although the various methods disclosed herein are described as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure. Furthermore, the methods may be implemented in association with the formation and/or processing of structures illustrated and described herein as well as in association with other structures not illustrated.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, the present disclosure has been described herein in the context of a particular implementation in a particular environment for a particular purpose. Those of ordinary skill in the art will recognize the usefulness is not limited thereto and the present disclosure may be beneficially implemented in any number of environments for any number of purposes. Thus, the claims set forth below are to be construed in view of the full breadth and spirit of the present disclosure as described herein.

What is claimed is:

1. A shuttle pump system, comprising:
   a pump chamber;
   a valve operable with the pump chamber;
   a wire coupled to a valve shaft of the valve for controlling a position of the valve;
   a pin disposed within an inset pathway of a cam, wherein the pin is moveable between multiple positions of the inset pathway in response to actuation of the valve shaft;
   a piston grip coupled to the valve shaft by the pin within the inset pathway;
   a base; and
   a cam block disposed within a slot of the base, the cam block including the inset pathway, wherein the piston grip is further coupled to the cam block.

2. The shuttle pump system of claim 1, wherein the wire is a shape memory alloy (SMA) wire.

3. The shuttle pump system of claim 1, the inset pathway comprising one or more sloped surfaces extending to an elevation drop off feature.

4. A shuttle pump system, comprising:
   a pump chamber;
   a valve operable with the pump chamber;
   a wire coupled to a valve shaft of the valve for controlling a position of the valve;
   a ball bearing within a housing, the ball bearing coupled to the wire and a track within the housing, wherein the ball bearing is moveable between multiple positions on the track in response to actuation of the valve shaft; and
   at least one gate operable between an open position and a closed position, wherein movement of the ball bearing on the track is restricted when the gate is in the closed position.

5. A valve assembly, comprising:
   a valve operable with a pump chamber;
   a wire coupled to a valve shaft of the valve for controlling a position of the valve;
   a piston grip including a pin disposed within an inset pathway of a cam, wherein the pin is moveable between multiple positions of the inset pathway in response to actuation of the valve shaft, and wherein the piston grip is coupled to the valve shaft;
   a base; and
   a cam block disposed within a slot of the base, the cam block including the inset pathway, wherein the piston grip is further coupled to the cam block.

6. The valve assembly of claim 5, wherein the wire is a shape memory alloy (SMA) wire.

7. The valve assembly of claim 5, the inset pathway comprising one or more sloped surfaces extending to an elevation drop off feature.

8. A wearable drug delivery system, comprising:
   a pump chamber;
   a valve operable to control a fluid entering or exiting the pump chamber;
   a wire coupled to a valve shaft of the valve for controlling a position of the valve, wherein the wire is a shape memory alloy (SMA) wire;
   a pin disposed within an inset pathway of a cam, wherein the pin is moveable between multiple positions of the inset pathway in response to actuation of the valve shaft;
   a piston grip coupled to the valve shaft by the pin within the inset pathway
   a base; and
   a cam block disposed within a slot of the base, the cam block including the inset pathway, wherein the piston grip is further coupled to the cam block.

9. The wearable drug delivery system of claim 8, the inset pathway comprising one or more sloped surfaces extending to an elevation drop off feature.

\* \* \* \* \*